US012687550B2

(12) United States Patent
Wilshaw et al.

(10) Patent No.: US 12,687,550 B2
(45) Date of Patent: Jul. 21, 2026

(54) DIAGNOSIS OF STAGE B2 DMVD

(71) Applicant: BOEHRINGER INGELHEIM VETMEDICA GMBH, Ingelheim am Rhein (DE)

(72) Inventors: Jenny Joyce Wilshaw, St. Albans (GB); Adrian Boswood, London (GB)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 813 days.

(21) Appl. No.: 17/995,620

(22) PCT Filed: Apr. 6, 2021

(86) PCT No.: PCT/GB2021/050836
§ 371 (c)(1),
(2) Date: Oct. 6, 2022

(87) PCT Pub. No.: WO2021/205152
PCT Pub. Date: Oct. 14, 2021

(65) Prior Publication Data
US 2023/0314449 A1 Oct. 5, 2023

(30) Foreign Application Priority Data
Apr. 7, 2020 (GB) ..................................... 2005110

(51) Int. Cl.
*G16H 50/20* (2018.01)
*G01N 33/68* (2006.01)
(52) U.S. Cl.
CPC ......... *G01N 33/6893* (2013.01); *G16H 50/20* (2018.01); *G01N 2800/325* (2013.01); *G01N 2800/56* (2013.01)

(58) Field of Classification Search
CPC ......... G01N 33/6893; G01N 2800/325; G01N 2800/56; G16H 50/20
See application file for complete search history.

(56) References Cited

FOREIGN PATENT DOCUMENTS

WO     WO-2015035155 A1 * 3/2015     .............. A61P 13/12
WO     WO 2020/037248     2/2020

OTHER PUBLICATIONS

Fox et al. "Pathology of myxomatous mitral valve disease in the dog," Journal of Veterinary Cardiology, 2012, vol. 14, No. 1, pp. 103-126.
Egenvall et al. "Mortality in over 350,000 insured Swedish dogs from 1995-2000: II. Breed-specific age and survival patterns and relative risk for causes of death," Acta Vet Scand., 2005, vol. 46, No. 3, pp. 121-136.
Mattin et al. "Degenerative mitral valve disease: Survival of dogs attending primary-care practice in England," Preventive Veterinary Medicine, Dec. 2015, vol. 122, No. 4, pp. 436-442.

(Continued)

*Primary Examiner* — Uzma Alam
*Assistant Examiner* — Fain Polyzos Boosalis
(74) *Attorney, Agent, or Firm* — Sheridan Ross P.C.

(57) ABSTRACT

The invention relates to method of diagnosing stage B2 degenerative mitral valve disease (DMVD) in a dog, a method of determining the probability of a dog having stage B2 DMVD, a method of training a model to predict stage B2 DMVD in a dog, and a related computer program and system.

18 Claims, 7 Drawing Sheets

(56) References Cited

OTHER PUBLICATIONS

Keene et al. "ACVIM consensus guidelines for the diagnosis and treatment of myxomatous mitral valve disease in dogs," Journal of Veterinary Internal Medicine, May 2019, vol. 33, No. 3, pp. 1127-1140.

Boswood et al. "Effect of Pimobendan in Dogs with Preclinical Myxomatous Mitral Valve Disease and Cardiomegaly: The EPIC Study—A Randomized Clinical Trial," Journal of Veterinary Internal Medicine, 2016, vol. 30, pp. 1765-1779.

Patronek et al. "Comparative Longevity of Pet Dogs and Humans: Implications for Gerontology Research," Journal of Gerontology: Biological Sciences, May 1997, vol. 52A, No. 3, pp. B171-B178.

Boswood et al. "Longitudinal Analysis of Quality of Life, Clinical, Radiographic, Echocardiographic, and Laboratory Variables in Dogs with Preclinical Myxomatous Mitral Valve Disease Receiving Pimobendan or Placebo: The EPIC Study," Journal of Veterinary Internal Medicine, 2018, vol. 32, pp. 72-85.

Borgarelli et al. "Survival Characteristics and Prognostic Variables of Dogs with Preclinical Chronic Degenerative Mitral Valve Disease Attributable to Myxomatous Degeneration," J Vet Intern Med, 2012, vol. 26, No. 1, pp. 69-75.

Mattin et al. "Factors associated with disease progression in dogs with presumed preclinical degenerative mitral valve disease attending primary care veterinary practices in the United Kingdom," Journal of Veterinary Internal Medicine, Mar./Apr. 2019, vol. 33, No. 2, pp. 445-454.

Eriksson et al. "Increased NT-proANP predicts risk of congestive heart failure in Cavalier King Charles spaniels with mitral regurgitation caused by myxomatous valve disease," Journal of Veterinary Cardiology, Sep. 2014, vol. 16, No. 3, pp. 141-154.

Pedersen et al. "Auscultation in Mild Mitral Regurgitation in Dogs: Observer Variation, Effects of Physical Maneuvers, and Agreement with Color Doppler Echocardiography and Phonocardiography," J Vet Intern Med, Jan. 1999, vol. 13, No. 1, pp. 56-64.

Haggstrom et al. "Heart Sounds and Murmurs: Changes Related to Severity of Chronic Valvular Disease in the Cavalier King Charles Spaniel," Journal of Veterinary Internal Medicine, Mar.-Apr. 1995, vol. 9, No. 2, pp. 75-85.

Ljungvall et al. "Use of signal analysis of heart sounds and murmurs to assess severity of mitral valve regurgitation attributable to myxomatous mitral valve disease in dogs," AJVR, May 2009, vol. 70, No. 5, pp. 604-613.

Ljungvall et al. "Murmur intensity in small-breed dogs with myxomatous mitral valve disease reflects disease severity," Journal of Small Animal Practice, Nov. 2014, vol. 55, No. 11, pp. 545-550.

Kvart et al. "Efficacy of Enalapril for Prevention of Congestive Heart Failure in Dogs with Myxomatous Valve Disease and Asymptomatic Mitral Regurgitation," J Vet Intern Med, 2002, vol. 16, No. 1, pp. 80-88.

Oyama et al. "Perceptions and priorities of owners of dogs with heart disease regarding quality versus quantity of life for their pets," JAVMA, Jul. 2008, vol. 233, No. 1, pp. 104-108.

Chetboul et al. "Observer-dependent variability of quantitative clinical endpoints: the example of canine echocardiography," J. Vet. Pharmacol. Therap., Feb. 2004, vol. 27, No. 1, pp. 49-56.

Moonarmart et la. "N-terminal pro B-type natriuretic peptide and left ventricular diameter independently predict mortality in dogs with mitral valve disease," Journal of Small Animal Practice, Feb. 200, vol. 51, No. 2, pp. 84-96.

Serres et al. "Plasma N-terminal pro-B-type natriuretic peptide concentration helps to predict survival in dogs with symptomatic degenerative mitral valve disease regardless of and in combination with the initial clinical status at admission," Journal of Veterinary Cardiology, Dec. 2009, vol. 11, No. 2, pp. 103-121.

Oyama et al. "Cardiac Troponin-I Concentration in Dogs with Cardiac Disease," J Vet Intern Med, 2004, vol. 18, No. 6, pp. 831-839.

Spratt et al. "Cardiac troponin I: evaluation of a biomarker for the diagnosis of heart disease in the dog," Journal of Small Animal Practice, Mar. 2005, vol. 46, pp. 139-145.

Ljungvall et al. "Cardiac Troponin I Is Associated with Severity of Myxomatous Mitral Valve Disease, Age, and C-Reactive Protein in Dogs," J Vet Intern Med, Jan. 2010, vol. 24, No. 1, pp. 153-159.

Hezzell et al. "The Combined Prognostic Potential of Serum High-Sensitivity Cardiac Troponin I and N-Terminal pro-B-Type Natriuretic Peptide Concentrations in Dogs with Degenerative Mitral Valve Disease," J Vet Intern Med, 2012, vol. 26, No. 2, pp. 302-311.

Mattin et al. "Prognostic factors in dogs with presumed degenerative mitral valve disease attending primary-care veterinary practices in the United Kingdom," Journal of Veterinary Internal Medicine, Mar. 2019, vol. 33, No. 2, pp. 432-444.

Peduzzi et al. "A Simulation Study of the Number of Events per Variable in Logistic Regression Analysis," J Clin Epidemiol, Dec. 1996, vol. 49, No. 12, pp. 1373-1379.

Chapman et al. "A Laboratory Diagnostic Approach to Hepatobiliary Disease in Small Animals," Vet Clin Small Anim, 2013, vol. 43, pp. 1209-1225.

Levine "Notes on the Gradation of the Intensity of Cardiac Murmurs," JAMA, Jul. 1961, vol. 177, No. 4, p. 261.

"Body Condition Scoring (BCS) Systems," Journal of the American Animal Hospital Association, 2010, 1 page.

Hansson et al. "Left Atrial to Aortic Root Indices Using Two-Dimensional and M-Mode Echocardiography in Cavalier King Charles Spaniels With and Without Left Atrial Enlargement," Veterinary Radiology & Ultrasound, 2002, vol. 43, No. 6, pp. 568-575.

Thomas et al. "Recommendations for Standards in Transthoracic Two-Dimensional Echocardiography in the Dog and Cat," Veterinary Radiology & Ultrasound, May 1994, vol. 35, No. 3, pp. 173-178.

Cornell et al. "Allometric Scaling of M-Mode Cardiac Measurements in Normal Adult Dogs," J Vet Intern Med, 2004, vol. 18, No. 1, pp. 311-321.

Buchanan et al. "Vertebral scale system to measure canine heart size in radiographs," JAVMA, Jan. 1995, vol. 206, No. 2, pp. 194-199.

Hansson et al. "Interobserver Variability of Vertebral Heart Size Measurements in Dogs With Normal and Enlarged Hearts," Veterinary Radiology & Ultrasound, 2005, vol. 46, No. 2, pp. 122-130.

Royston et al. "Multivariable Model-Building: A pragmatic approach to regression analysis based on fractional polynomials for modelling continuous variables," John Wiley & Sons Ltd., 2008, pp. i-10.

Delong et al. "Comparing the Areas Under Two or More Correlated Receiver Operating Characteristic Curves: A Nonparametric Approach," Biometrics, Sep. 1988, vol. 44, No. 3, pp. 837-845.

Hoerl et al. "Ridge Regression: Biased Estimation for Nonorthogonal Problems," Technometrics, Feb. 1970, vol. 12, No. 1, pp. 55-67.

Cortes et al. "Support-Vector Networks," Machine Learning, Sep. 1995, vol. 20, No. 3, pp. 273-297.

Breiman "Random Forests," Machine Learning, 2001, vol. 45, No. 1, pp. 5-32.

Chen et al. "XGBoost: A Scalable Tree Boosting System," Proceedings of the ACM SIGKDD International Conference on Knowledge Discovery and Data Mining, New York, New York, USA: Association for Computing Machinery, 2016, pp. 785-794.

Kulesa et al. "Sampling distributions and the bootstrap," Nature Methods, Jun. 2015, vol. 12, No. 6, pp. 477-478.

Steyerberg et al. "Assessing the Performance of Prediction Models A Framework for Traditional and Novel Measures," Epidemiology, Jan. 2010, vol. 21, No. 1, pp. 128-138.

Walsh et al. "Beyond discrimination: A comparison of calibration methods and clinical usefulness of predictive models of readmission risk," Journal of Biomedical Informatics, Dec. 2017, vol. 76, pp. 9-18.

Steyerberg et al. "Towards better clinical prediction models: seven steps for development and an ABCD for validation," European Heart Journal, Aug. 2014, vol. 35, No. 29, pp. 1925-1931.

Bonnett et al. "Guide to presenting clinical prediction models for use in clinical settings," BMJ, Apr. 2019, vol. 365, Article 1737, 8 pages.

(56) References Cited

OTHER PUBLICATIONS

Lopez-Alvarez et al. "Clinical Severity Score System in Dogs with Degenerative Mitral Valve Disease," Journal of Veterinary Medicine, 2015, vol. 29, pp. 575-581.

Collins et al. "External validation of multivariable prediction models: a systematic review of methodological conduct and reporting," BMC Medical Research Methodology, 2014, vol. 14, No. 1, Article 40, 11 pages.

Hezzell et al. "Selected echocardiographic variables change more rapidly in dogs that die from myxomatous mitral valve disease," Journal of Veterinary Cardiology, 2012, vol. 14, pp. 269-279.

Chetboul et al. "Association of Plasma N-Terminal Pro-B-Type Natriuretic Peptide Concentration with Mitral Regurgitation Severity and Outcome in Dogs with Asymptomatic Degenerative Mitral Valve Disease," J Vet Intern Med, 2009, vol. 23, pp. 984-994.

Oyama et al. "Clinical usefulness of an assay for measurement of circulating N-terminal pro-B-type natriuretic peptide concentration in dogs and cats with heart disease," JAVMA, Jul. 2013, vol. 243, No. 1, pp. 71-82.

Kellihan et al. "Weekly variability of plasma and serum NT-proBNP measurements in normal dogs," Journal of Veterinary Cardiology, May 2009, vol. 11, Suppl 1, pp. S93-S97.

Winter et al. "Biologic variability of N-terminal pro-brain natriuretic peptide in healthy dogs and dogs with myxomatous mitral valve disease," Journal of Veterinary Cardiology, Apr. 2019, vol. 19, No. 2, pp. 124-131.

Hoglund et al. "Low intensity heart murmurs in boxer dogs: inter-observer variation and effects of stress testing," Journal of Small Animal Practice, Apr. 2004, vol. 45, No. 4, pp. 178-185.

Keren et al. "Evaluation of a Novel Method for Grading Heart Murmur Intensity," Arch Pediatr Adolesc Med, Apr. 2003, vol. 159, No. 4, pp. 329-334.

Fudim et al. "Pathophysiology and Treatment Options for Cardiac Anorexia," Curr Heart Fail Rep, Jun. 2011, vol. 8, No. 2, pp. 147-153.

Fonfara et al. "Leptin Expression in Dogs with Cardiac Disease and Congestive Heart Failure," J Vet Intern Med, Sep. 2011, vol. 25, No. 5, pp. 1017-1024.

Adlbrecht et al. "Chronic heart failure leads to an expanded plasma volume and pseudoanaemia, but does not lead to a reduction in the body's red cell volume," European Heart Journal, 2008, vol. 29, No. 19, pp. 2343-2350.

Androne et al. "Hemodilution Is Common in Patients With Advanced Heart Failure," Circulation, Jan. 2003, vol. 107, No. 2, pp. 226-229.

Abramov et al. "Comparison of Blood Volume Characteristics in Anemic Patients With Low Versus Preserved Left Ventricular Ejection Fractions," Am J Cardiol., Oct. 2008, vol. 102, No. 8, pp. 1069-1072.

Duarte et al. "Prognostic Value of Estimated Plasma Volume in Heart Failure," JACC: Heart Failure, Nov. 2015, vol. 3, No. 11, pp. 886-893.

Dittrich et al. "Haemodilution improves organ function during normothermic cardiopulmonary bypass: investigations in isolated perfused pig kidneys," Perfusion, Jun. 2000, vol. 15, No. 3, pp. 225-229.

Horn et al. "Aging and the cardiac collagen matrix: Novel mediators of fibrotic remodelling," Journal of Molecular and Cellular Cardiology, 2016, vol. 93, pp. 175-185.

Hezzell et al. "Associations between N-terminal procollagen type III, fibrosis and echocardiographic indices in dogs that died due to myxomatous mitral valve disease," Journal of Veterinary Cardiology, Dec. 2014, vol. 16, No. 4, pp. 257-264.

Bay et al. "NT-proBNP: a new diagnostic screening tool to differentiate between patients with normal and reduced left ventricular systolic function," Heart, 2003, vol. 89, pp. 150-154.

Nikolaou et al. "Liver function abnormalities, clinical profile, and outcome in acute decompensated heart failure," European Heart Journal, Mar. 2013, vol. 34, No. 10, pp. 742-749.

Kubo et al. "Liver Function Abnormalities in Chronic Heart Failure: Influence of Systemic Hemodynamics," Arch Intern Med, Jul. 1987, vol. 147, No. 7, pp. 1227-1230.

Henriksen et al. "Increased circulating pro-brain natriuretic peptide (proBNP) and brain natriuretic peptide (BNP) in patients with cirrhosis: relation to cardiovascular dysfunction and severity of disease," Gut, Oct. 2003, vol. 52, No. 10, pp. 1511-1517.

Licata et al. "NT Pro BNP Plasma Level and Atrial Volume Are Linked to the Severity of Liver Cirrhosis," PLOS One, Aug. 2013, vol. 8, No. 8, Article e68364, 7 pages.

Cawley et al. "On Over-fitting in Model Selection and Subsequent Selection Bias in Performance Evaluation," Journal of Machine Learning Research, 2010, vol. 11, pp. 2079-2107.

Rajkomar et al. "Machine Learning in Medicine," The New England Journal of Medicine, Apr. 2019, vol. 380, No. 14, pp. 1347-1358.

Steyerberg et al. "Risk prediction with machine learning and regression methods," Biometrical Journal, Jul. 2014, vol. 56, No. 4, pp. 601-606.

Reagan et al. "Machine learning algorithm as a diagnostic tool for hypoadrenocorticism in dogs, " Domestic Animal Endocrinology, Jul. 2020, vol. 72, Article 106396, 9 pages.

Bradley et al. "Predicting early risk of chronic kidney disease in cats using routine clinical laboratory tests and machine learning," Journal of Veterinary Internal Medicine, Nov. 2019, vol. 33, No. 6, pp. 2644-2656.

Bille et al. "Risk of anaesthetic mortality in dogs and cats: an observational cohort study of 3546 cases," Veterinary Anaesthesia and Analgesia, 2012, vol. 39, No. 1, pp. 59-68.

Collins et al. "Sample size considerations for the external validation of a multivariable prognostic model: a resampling study," Statistics in Medicine, Jan. 2016, vol. 35, No. 2, pp. 214-226.

Riley et al. "External validation of clinical prediction models using big datasets from e-health records or IPD meta-analysis: Opportunities and challenges," BMJ, 2016, vol. 353, Article i3140, 11 pages.

Sevakula et al. "State-of-the-Art Machine Learning Techniques Aiming to Improve Patient Outcomes Pertaining to the Cardiovascular System," Journal of the American Heart Association, Feb. 2020, vol. 9, No. 4, 15 pages.

Vennemann et al. "Automated diagnosis of heart valve degradation using novelty detection algorithms and machine learning," PLOS One, Sep. 2019, vol. 14, No. 9, Article e0222983, 18 pages.

Ruaux et al. "Biologic variability in NT-proBNP and cardiac troponin-I in healthy dogs and dogs with mitral valve degeneration," Veterinary Clinical Pathology, Jun. 2015, vol. 44, No. 3, pp. 420-430.

Park et al. "Correlation between NT-proBNP and Lipase Levels according to the severity of chronic mural valve disease in dogs," Journal of Veterinary Science, Jul. 2019, vol. 20, No. 4, article e43, 8 pages.

Hosmer et al. "Model-Building Strategies and Methods for Logistic Regression," Applied Logistic Regression, 2013, Third Edition, Chapter 4, pp. 89-151.

ZHANG "Model building strategy for logistic regression: purposeful selection," Ann Transl Med, 2016, vol. 4, No. 6, Article 111, 7 pages.

* cited by examiner

5a.

5b.

5c.

5d.

DIAGNOSIS OF STAGE B2 DMVD

CROSS REFERENCE TO RELATED APPLICATIONS

This application is a national stage application under 35 U.S.C. 371 and claims the benefit of PCT Application No. PCT/GB2021/050836 having an international filing date of 6 Apr. 2021, which designated the United States, which PCT application claimed the benefit of Great Britain Application No. 2005110.8 filed 7 Apr. 2020, the disclosures of each of which are incorporated herein by reference in their entireties.

FIELD OF THE INVENTION

The invention relates to method of diagnosing stage B2 degenerative mitral valve disease (DMVD) in a dog, a method of determining the probability of a dog having stage B2 DMVD, a method of training a model to predict stage B2 DMVD in a dog, and a related computer program and system.

BACKGROUND TO THE INVENTION

Degenerative mitral valve disease (DMVD) is an acquired condition characterised by progressive myxomatous degeneration of the mitral valve.[1] DMVD is the most prevalent cardiac disease of the adult dog[2] and it is estimated that it affects 3.5% of dogs seen in primary-care practice.[3] Dogs with DMVD experience a long, asymptomatic period, throughout which they may develop eccentric hypertrophy of the left sided chambers of the heart to compensate for chronic volume overload. These structural changes are used to identify dogs with more advanced preclinical disease in a staging scheme produced by the American College of Veterinary Internal Medicine (ACVIM).[4] Dogs are classified as being in stage B2 if echocardiographic measurements of left atrial and left ventricular size exceed established thresholds that are indicative of the presence of cardiomegaly. Correctly identifying stage B2 dogs is clinically important as the EPIC study (Effect of Pimobendan in Dogs with Preclinical Myxomatous Mitral Valve Disease and Cardiomegaly) demonstrated a clear benefit to medically managing these cases.[5] In the EPIC study, treatment with the drug pimobendan reduced the hazard of reaching the study's primary composite endpoint of congestive heart failure (CHF), cardiac related death or euthanasia by approximately one third. Given the average life expectancy of a dog,[6] prolongation of the preclinical phase of DMVD represents a marked extension of good quality life.[7]

It is challenging to recognise whether a patient is in stage B2 using only the parameters obtained from an external examination. Furthermore, factors related to the patient, owner and primary-care practice can affect access to echocardiography. To enable widespread implementation of treatment in accordance with the EPIC study, there is a need to identify dogs in stage B2 of DMVD without using echocardiography.

SUMMARY OF THE INVENTION

The present invention relates to the identification of dogs with stage B2 DMVD without using echocardiography. The present inventors have surprisingly identified that the probability of a dog having stage B2 DMVD is associated with parameters that can be easily and routinely assessed in primary-care veterinary practices.

A model based on the parameters can be used to generate an output value associated with the probability of a dog having stage B2 DMVD. In this way, dogs can be screened for stage B2 DMVD, to identify individuals likely to benefit from echocardiographic investigation. This may assist in the allocation of owner and practice resources. The output value may also be used to diagnose the presence or absence of B2 DMVD, in place of traditional echocardiographic measurements. This allows for disease staging in dogs without access to echocardiography.

By reducing the reliance on echocardiography to identify stage B2 DMVD, the findings of the EPIC study can be implemented more widely. That is, the present invention facilitates the identification of stage B2 in primary-care veterinary practices, and allows treatment to be advantageously initiated at this preclinical stage of disease.

Accordingly, the present invention provides a method of diagnosing stage B2 degenerative mitral valve disease (DMVD) in a dog, the method comprising the steps of: (a) receiving characteristic data relating to the dog, the characteristic data comprising two or more of: appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; (b) processing the characteristic data using a model, wherein the output of the model is an output value associated with the probability of the dog having stage B2 DMVD; and (c) diagnosing the presence or absence of stage B2 DMVD based on a comparison of the output value to a predetermined value.

The present invention also provides:

a method of screening for stage B2 DMVD in a dog, the method comprising the steps of: (a) receiving characteristic data relating to the dog, the characteristic data comprising two or more of: appetite, BCS, creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; and (b) processing the characteristic data using a model, wherein the output of the model is an output value associated with the probability of the dog having stage B2 DMVD;

a method of training a model to predict stage B2 DMVD in a dog, the method comprising: (i) processing characteristic data relating to a dog using the model to output an output value, the characteristic data comprising two or more of: appetite, BCS, creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; (ii) comparing the output value to a diagnosis of presence or absence of stage B2 DMVD in the dog; and (iii) adjusting the parameters of the model based on the result of the comparison;

a computer program comprising code means that, when executed by a computer system, instructs the computer system to perform the method of any one of the preceding claims; and a system for diagnosing stage B2 DMVD in dogs, the system comprising: an input device configured to receive characteristic data relating to a dog, the characteristic data comprising two or more of: appetite, BCS, creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; a model configured to receive the characteristic data and generate an output value associated with the probability of the dog having stage B2 DMVD; and an output device configured to output the output value.

BRIEF DESCRIPTION OF THE FIGURES

FIG. 3: Discriminatory performance of the explanatory multivariable logistic regression model when applied to the clean, complete and excluded populations. The area under the receiver operating characteristic curves were as follows: for the clean population 0.84 (0.82-0.87); for the complete population 0.81 (0.79-0.83); for the excluded population 0.76 (0.72-0.80).

FIG. 4: Discriminatory performance of the explanatory multivariable logistic regression model in comparison to using NT-proBNP alone or the vertebral heart score. The area under the receiver operating characteristic curves were as follows: multivariable logistic regression model 0.84 (0.82-0.87); univariable NT-proBNP model 0.77 (0.74-0.80); univariable vertebral heart score model 0.76 (0.69-0.83). NT-proBNP, N-terminal propeptide of B-type natriuretic peptide; VHS, vertebral heart score.

DETAILED DESCRIPTION OF THE INVENTION

Method of Screening

Figure 1:
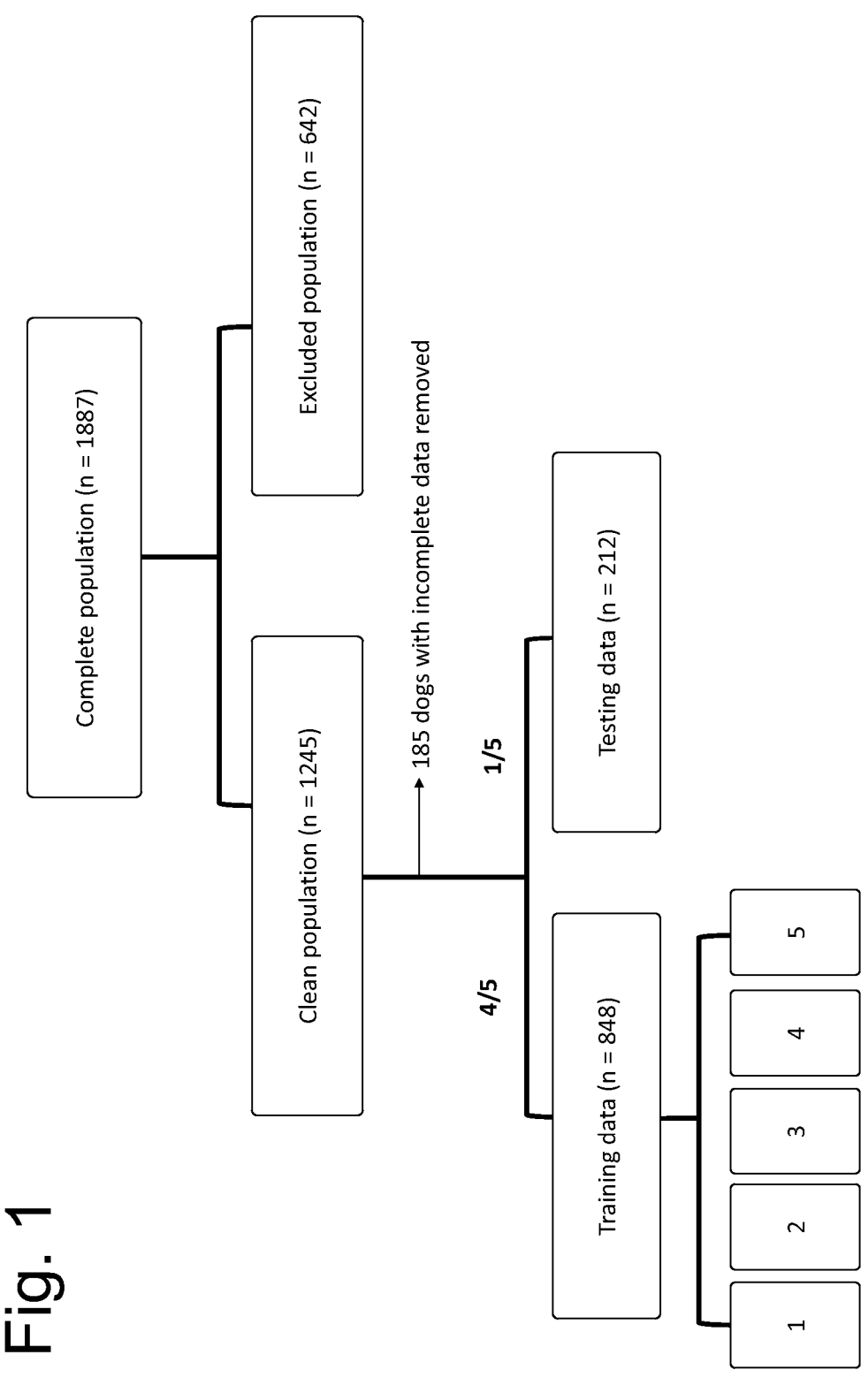
FIG. 1: A flow chart indicating how data were partitioned prior to their inclusion in analyses.

The present invention provides a method of screening for stage B2 DMVD in a dog, the method comprising the steps of: (a) receiving characteristic data relating to the dog, the characteristic data comprising two or more of: appetite, BCS, creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; and (b) processing the characteristic data using a model, wherein the output of the model is an output value associated with the probability of the dog having stage B2 DMVD.

The method of screening advantageously permits the probability of a dog having stage B2 DMVD to be identified without using echocardiography. Traditionally, dogs are classified as being in stage B2 if echocardiographic measurements of left atrial and left ventricular size exceed established thresholds that are indicative of the presence of cardiomegaly. However, echocardiography requires special equipment. Many primary-care veterinary practices do not possess the necessary equipment to perform echocardiography. Furthermore, the performance of echocardiography and analysis of results requires specialist skills which are not commonplace among veterinarians employed in primary-care practices. Referral of patients to specialist facilities is thus often required to identify stage B2 DMVD. This can prove time-consuming and costly, and often requires patients and their owners to travel. In some cases, these factors preclude dogs from accessing echocardiography. If stage B2 DVMD cannot be identified, it is difficult to know when treatment should be implemented.

The method of screening helps to overcome these issues. The method allows the probability of a dog having stage B2 DMVD to be identified without the need for echocardiography. The method generates an output value associated with the probability of a dog having stage B2 DMVD. The output value can be used to inform clinical decisions. For example, the output value can be used to identify dogs in which echocardiography is particularly indicated. That is, dogs having an output value associated with a high probability of having stage B2 DMVD may be prioritised for echocardiography to confirm the presence (or absence) of B2 DMVD. Treatment may be implemented depending on the outcome of echocardiography. Dogs with a low probability of stage B2 DMVD are less likely to show abnormalities upon echocardiography. An output value associated with a low probability of stage B2 DMVD may therefore indicate that echocardiography may be of little benefit to a particular dog. In addition, it may discourage the use of medications where these are not indicated due to potential adverse effects. By prioritising cases for echocardiography, owner and practice resources can be conserved. Individual dogs may be subject to fewer clinical interventions.

Dogs

The method is used to screen for stage B2 DMVD in a dog. The dog may be a domestic dog (*Canis familiaris*) or any other member of the genus *Canis*.

The dog may have, or be presumed to have, DVMD. The dog may have received a diagnosis (or presumptive diagnosis) of DMVD prior to step (a) of the method. The diagnosis (or presumptive diagnosis) may, for example, be based on the signalment of the dog. For example, a dog of a certain breed and/or age may be suspected to have DMVD. The diagnosis (or presumptive diagnosis) may, for example, be based on the presence of a left apical systolic murmur. Preferably, the diagnosis (or presumptive diagnosis) is based on the presence of a left apical systolic murmur in a dog of a certain age and/or breed. At-risk breeds and ages are well-known in the art.

The DVMD is preferably preclinical. That is, the dog is preferably not in congestive heart failure. Congestive heart failure may be indicated by radiographic, historical and/or physical examination findings. Preferably, the dog has not received treatment with a loop diuretic prior to the method. In asymptomatic or preclinical DMVD, physiological changes compensate for mitral valve insufficiency.

The dog may be of any age. For example, the dog may be at least one, at least two, at least, three, at least four, at least five, at least 6, at least 7, at least 8, at least 9, at least 10, at least 11, or at least 12 years old. Preferably, the dog is at least 6 years old. DVMD is an acquired disease and patients typically develop it in adult life as they age. The dog may be of any breed. The dog may, for example, be a cavalier king charles spaniel, a jack russell terrier, a chihuahua, a cocker spaniel or a shih tzu.

The dog may be of any sex. The dog may be male entire. The dog may be female entire. The dog may be male neutered. The dog may be female neutered.

The dog may be of any weight. For example, the dog may weigh at least 1 kg, at least 2 kg, at least 5 kg, at least 10 kg, at least 15 kg, at least 20 kg, at least 25 kg, or at least 30 kg. The dog may weigh between 1 kg and 70 kg, such as between 2 kg and 65 kg, between 5 kg and 60 kg, between 10 kg and 55 kg, between 15 kg and 50 kg, between 20 kg and 45 kg, between 30 kg and 40 kg, or between 30 kg and 35 kg. Preferably, the dog weighs between 2 kg and 25 kg. Typically, DVMD is a condition of small breed dogs.

Preferably, the dog has not received treatment with selected cardiac medications prior to step (a) of the method. These include: pimobendan , loop diuretics (e.g. furosemide) and anti-arrhythmic medications. The cardiac medications prescribed to a dog will be apparent from its clinical history.

Characteristic Data

The method of screening comprises receiving characteristic data relating to the dog being screened for stage B2 DVMD. The characteristic data comprises two or more of: appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration, in any combination. For example, the characteristic data may comprise three or more, four or more, five or more, six or more, seven or more, eight or more, nine or more, 10 or more, 11 or more, 12 or more, 13 or more, 14 or more, 15 or more, 16 or more , 17 or more, 18 or more, 19 or more, 20 or more, 21 or more, 22 or more, 23 or more, 24 or more, 25 or more, 26 or more, 27 or more, 28 or more, 29 or more, or 30 or more of: appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration, in any combination.

The characteristic data may, for example, comprise two or more of (i) appetite, (ii) body condition score (BCS), (iii) creatinine concentration, (iv) murmur intensity, and (v) NT-ProBNP concentration. For example, the characteristic data may comprise: (i) and (ii); (i) and (iii); (i) and (iv); (i) and (v); (ii) and (iii); (ii) and (iv); (ii) and (v); (iii) and (iv); (iii) and (v); (iv) and (v); (i), (ii),and (iii); (i), (ii) and (iv); (i), (ii) and (v); (i), (iii) and (iv); (i), (iii) and (v); (i), (iv) and (v); (ii), (iii) and (iv); (ii), (iii) and (v); (ii), (iv) and (v); (iii), (iv) and (v); (i), (ii) and (iii), (iv); (i), (ii), (iii) and (v); (i), (ii), (iv) and (v); (i), (iii), (iv) and (v); (ii), (iii), (iv) and (v); or (i), (ii), (iii), (iv) and (v).

Preferably, the characteristic data comprises NT-ProBNP concentration. The characteristic data may, for example, comprise NT-proBNP concentration, appetite, creatinine concentration and murmur intensity. For instance, the characteristic data may comprise NT-proBNP concentration, appetite, creatinine concentration, murmur intensity and BCS.

When the model used to process the characteristic data is derived using a regression process (such as multivariable logistic regression or regularised regression), the characteristic data may preferably comprise: NT-proBNP concentration, appetite, creatinine concentration, and murmur intensity; or NT-proBNP concentration, appetite, creatinine concentration, murmur intensity and BCS.

The characteristic data may comprise all of appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration.

When the model is derived using a machine learning process (such as a support vector machines (SVM) process, a random forest process, or a gradient boosting process), or regularised regression, the characteristic data may preferably comprise all of appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration.

Each type of characteristic data can easily be assessed in primary-care practice using methods routine in the art.

Appetite may be assessed by visual monitoring for changes in appetite over a period of time, for example by a primary-care practitioner or the owner of a dog. The period of time may, for example, be one week, two weeks, three weeks, four weeks, one month, two months, three months, four months, five months, or six months. The period of time may, for example, be one week to one year, such as two weeks to 11 months, three weeks to 10 months, four weeks to 9 months, one month to eight months, two months to seven months, three months to six months, or for months to five months. The period of time may be six months. The period of time may be one month to six months, such as one month to three months. Appetite may be scored, for example, as "reduced" or "normal"

Body condition score (BCS) may be scored using the American Animal Hospital Association's 9 point scale (*American Animal Hospital Association. Canine Body Condition Score for* 1-9 *and* 1-5 *Scales*. Veterinary Forensics: Animal Cruelty Investigations. 2013.) The scale uses visual indicators and the results of palpation to characterise the body condition (e.g. muscle mass, fat reserves) of the individual. Body condition may indicate whether or not an individual dog is healthy weight, overweight, or underweight. For example, a BCS of 3 or less may indicate that the dog is underweight. A BCS of 6 or more may indicate that dog is overweight. A BCS of 4 or 5 may indicate that the dog is a healthy weight.

DVMD is associated with a characteristic heart murmur. Dogs with DVMD typically have a left apical systolic murmur with a point of maximum intensity over the mitral valve. Murmur intensity may be assessed using the Levine scale (Levine S A. *Notes on the Gradation of the Intensity of Cardiac Murmurs*. JAMA J Am Med Assoc. 1961 Jul. 29; 177(4): 261), which attributes the murmur a grade of I to VI based on its audibility upon cardiac auscultation. The grade attributed by the Levine scale may be reclassified, for instance to reduce the complexity of the method. For example grade I and II murmurs may be classified as "soft". Grade III murmurs may be classified as "moderate". Grade IV murmurs may be classified as "loud". Grade V and VI murmurs may be classified as "thrilling". Murmur intensity may be assessed using a simplified scale, where murmurs are classified as soft, moderate, loud or thrilling based on audibility upon cardiac auscultation.

The age of the dog is typically measured in years. To reduce the complexity of the method, the age of the dog may be classified in terms of a particular age range (for example: less than 8 years, 8 to 10 years, 10 to 12 years, or greater than 12 years).

Breed may be assessed by visual examination, or by reference to a dog's pedigree. Dog breeds are well-known in the art, and breed can easily be determined by the skilled person. DMVD is most common in small breeds, with some breeds (such as Cavalier King Charles spaniels (CKCS) being highly predisposed).

Cardiac medications include, for example, pimobendan, angiotensin-converting enzyme (ACE) inhibitors and diuretics. ACE inhibitors include, for example, benazepril and enalapril. Diuretics include, for example, loop diuretics (e.g. furosemide) and potassium-sparing diuretics (e.g. spironolactone). The cardiac medications prescribed to a dog will be apparent from its clinical history.

The sex of the dog will be apparent from physical examination and/or the dog's clinical history. Sex may be classified as male entire, female entire, male neutered, or female neutered.

Cough may be assessed by visual monitoring for the presence or absence of a cough, for example by a primary-care practitioner or the owner of a dog. Cough may, for example, be classified as "present" or "absent".

Exercise tolerance is the ability to perform physical exercise at what would be considered to be a normally expected level or duration for an individual. Exercise tolerance may be assessed by visual monitoring for changes in exercise tolerance over a period of time, for example by a primary-care practitioner or the owner of a dog. The period of time may, for example, be one week, two weeks, three weeks, four weeks, one month, two months, three months, four months, five months, or six months. The period of time may, for example, be one week to one year, such as two weeks to 11 months, three weeks to 10 months, four weeks to 9 months, one month to eight months, two months to seven months, three months to six months, or for months to five months. The period of time may be six months. The period of time may be one month to six months, such as one month to three months. Exercise tolerance may be scored, for example, as "reduced" or "normal".

Heart rate may be measured in beats per minute. Heart rate is typically measured, by, for example, cardiac auscultation. Heart rate can also be measured by, for example, manually taking the dog's pulse, using pulse oximetry, or using ECG.

Heart rhythm is typically assessed by cardiac auscultation. ECG may also be used to assess heart rhythm. Heart rhythm may be classified based on the predominant heart rhythm throughout the observation period. For example, heart rhythm may be classified as "sinus rhythm", "sinus arrhythmia" or "other".

Respiratory rate may be measured in breaths per minute. Respiratory rate is typically measured by, for example, observation of the dog or thoracic auscultation.

Creatinine concentration, alanine aminotransferase (ALT) activity, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, sodium concentration and cTnI concentration can be measured in a sample obtained from the dog using assays routine in the art. Results that fall below the detection limits of the assay may assigned the value of the lower limit. Results that fall above the detection limits of the assay may assigned the value of the upper limit. The sample may be a blood sample, such as a venous blood sample. The sample may be a serum sample. The serum sample may be obtained by processing a blood sample, such as a venous blood sample.

NT-proBNP concentration can be measured in a sample obtained from the dog using assays routine in the art. Results that fall below the detection limits of the assay may assigned the value of the lower limit. Results that fall above the detection limits of the assay may assigned the value of the upper limit. The sample may be a blood sample, such as a venous blood sample. The sample may be a plasma sample. The plasma sample may be obtained by processing a blood sample, such as a venous blood sample.

Any of the characteristic data may transformed prior to step (a). For example, characteristic data relating to continuous variables (such as heart rate, respiratory rate, creatinine concentration, alanine aminotransferase (ALT) activity, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, sodium concentration, cTnI concentration and NT-proBNP concentration) may be transformed (for instance, logarithmically transformed), scaled or categorised (for instance, into quartiles). Characteristic data relating to categorical (such as appetite, BCS, murmur intensity, age, breed, sex, cough, and exercise tolerance) variables may be reclassified into broader levels.

Models

The method of screening comprises processing characteristic data using a model. The model may be an algorithm that performs a number of processing steps on the characteristic data and produces an output. One or more of the processing steps may produce a sub-output that is used by the model in the next processing step. One or more of the processing steps may be performed in parallel.

Processing of the characteristic data may include performing mathematical calculations on the characteristic data. For example, the model may use one or more of the characteristic data as an input in a linear function to calculate an output.

Processing of the characteristic data may include performing classification steps using the characteristic data. The model may use one or more of the types of characteristic data to perform a classification step. The classification step may be a binary classification step that produces an output associated with one of two categories based on the one or more types of the characteristic data. The classification step may produce an output associated with one of more than two categories.

The model may be derived using a regression process. In a regression process, characteristic data associated with a plurality of dogs previously either diagnosed with stage B2

DVMD or not diagnosed with stage B2 DVMD may be analysed to derive a relationship between a set of characteristic data and the presence of stage B2 DVMD.

The model may be derived using multivariable logistic regression. Logistic regression is a regression process that uses a logistic function to associate one or more input variables with a prediction of the likelihood of an output variable. One or more of the types of characteristic data may be used as input variables and the output variable may be a value associated with the likelihood that the dog associated with the set of characteristic data has stage B2 DVMD. The logistic function may be based upon the coefficients in Table 6:

For a dog with the following characteristics: decreased appetite, yes; body condition score, 5; creatinine, C; murmur, moderate; $\log_{10}$(NT-proBNP), NT.

$$Odds=Exp[-10+(2.99)+(-1.39)+(-0.02 \times C)+(0.73)+ (3.66 \times NT)] Predicted \ probability=Odds/[1+ Odds]$$

The model may be derived using regularised regression. Regularised regression is a regression process that adds a penalty function to the least squares fitting process being used to derive a linear function that relates the one or more types of characteristic data and the value associated with the likelihood that the dog associated with the set of characteristic data has stage B2 DVMD. The regularised regression process may be a ridge regression process. An exemplary linear relationship is set out in Example 2.

The model may be derived using a machine learning process. In a machine learning process, characteristic data associated with a dog that has stage B2 DVMD or does not have stage B2 DVMD may be processed by an untrained model using a set of starting conditions. The starting conditions may be determined randomly. Alternatively, one or more of the starting conditions may be predetermined. The output of the untrained model may be compared with the condition of the dog associated with the characteristic data and the processing by the untrained model may be adjusted based on the comparison. This process may be repeated until the output of the model is associated with an accurate prediction of whether a dog associated with a particular set of characteristic data has stage B2 DVMD. This process may be referred to as a training process. The regression processes described above may also be arrived at using a training process.

The model may be derived using a support vector machines (SVM) process. In a SVM process, characteristic data associated with a dog may be represented as a vector defined by each of the variables making up the characteristic data. A model derived using an SVM process compares the location of the vector specified by the characteristic data to a hyperplane. Depending on the location of the vector in relation to the hyperplane, the model may classify the characteristic data as being associated with a dog having stage B2 DVMD or associated with a dog not having stage B2 DVMD. During the training process of a SVM model, the position of the hyperplane is modified to maximize the distance between the hyperplane and the location of the closest vector associated with a dog having stage B2 DVMD and the distance between the hyperplane and the location of the closest vector associated with a dog not having stage B2 DVMD.

The model may be derived using a random forest process. In a random forest process, a plurality of decision trees is created that classify characteristic data as associated with a dog having stage B2 DVMD or associated with a dog not having stage B2 DVMD.

Each decision tree may have a number of steps where a sub-classification is made based on a variable of the characteristic data. For example, a sub-classification may be made if a variable is more than or less than a particular value. Based on the combination of sub-classifications, each decision tree arrives at the classification of the characteristic data. The classification arrived at by a model derived by a random forest process may be based on a combination of the classification made by the plurality of decision trees. For example, the modal classification or average class probability may be used. During the training process of a model derived using a random forest process, the set of training data and types of characteristic data used by each decision tree may be selected randomly.

A gradient boosting process may be used when deriving the model. For example, in the random forest process, the accuracy of each generated decision tree may be used as an input when determining the parameters of the next decision tree. The XGBoost algorithm is an example of a machine learning process that may be used to derive the model using a gradient boosting process.

Output Values

The output of the model is an output value that is associated with the probability of the dog having stage B2 DMVD. The output value may be a discrete variable or a continuous variable. For example, the output value may be a classification that either the characteristic data used as an input for the model is associated with a dog that has stage B2 DVMD or is associated with a dog that does not has stage B2 DVMD. The output value may be a variable that is associated with the probability that the characteristic data used as an input for the model is associated with a dog that has stage B2 DVMD. The output value may be equal to the probability of the dog having stage B2 DMVD. The output value may not be equal to the probability of the dog having stage B2 DMVD and processing of the output value may be performed to obtain the output value. For example, the output value may a function of the probability of the dog having stage B2 DMVD, such as its inverse.

Method of Diagnosis

The present invention provides a method a method of diagnosing stage B2 degenerative mitral valve disease (DMVD) in a dog, the method comprising the steps of: (a) receiving characteristic data relating to the dog, the characteristic data comprising two or more of: appetite, body condition score (BCS), creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; (b) processing the characteristic data using a model, wherein the output of the model is an output value associated with the probability of the dog having stage B2 DMVD; and (c) diagnosing the presence or absence of stage B2 DMVD based on a comparison of the output value to a predetermined value.

The method of diagnosis advantageously permits the diagnosis of stage B2 DMVD without the need for echocardiography. As explained above, dogs are traditionally classified as being in stage B2 if echocardiographic measurements of left atrial and left ventricular size exceed established thresholds that are indicative of the presence of cardiomegaly. However, access to echocardiography may be restricted by factors related to the patient, owner and primary-care practice.

The method of the invention overcomes this issue by permitting diagnosis of stage B2 DMVD in the absence of echocardiography. The method generates an output value associated with the probability of a dog having stage B2 DMVD. The presence or absence of stage B2 DMVD may be diagnosed based on the output value. An output value below a certain threshold may indicate the absence of stage B2 DMVD. An output value above a certain threshold may indicate the presence of stage B2 DMVD. Treatment may be implemented if the output value indicates the presence of stage B2 DMVD. The output value generated by the method may thus be used in place of traditional echocardiographic measurement to diagnose the presence or absence of B2 DMVD. The method therefore makes DMVD staging more accessible. As a result, it is easier to implement treatment (for example, with pimobendan) at the preclinical B2 stage of disease, in accordance with the recommendations set out in the EPIC study.

Dogs, Characteristic Data, Models and Output Values

Dogs, characteristic data, models and output values are described in detail above in connection with a method of screening for stage B2 DMVD in a dog. Any of the aspects described in connection with a method of screening for stage B2 DMVD in a dog may apply to the method of diagnosing stage B2 DMVD in a dog.

Diagnosis of Stage B2 DMVD

The method of diagnosing stage B2 DMVD comprises diagnosing the presence or absence of stage B2 DMVD based on a comparison of the output value to a predetermined value.

The predetermined value may be a "threshold" output value that can be used to rule stage B2 DMVD in and/or out. For example, the presence of stage B2 DMVD may be indicated by an output value that is associated with a probability of the dog having stage B2 DMVD that is greater than or equal to the probability associated with the predetermined value. The absence of stage B2 DMVD may be indicated by an output value that is associated with a probability of the dog having stage B2 DMVD that is less than the probability associated with the predetermined value. The predetermined value for indicating the presence of stage B2 DMVD may be the same as the predetermined value for indicating the absence of stage B2 DMVD. The predetermined value for indicating the presence of stage B2 DMVD may be different from the predetermined value for indicating the absence of stage B2 DMVD.

The presence of stage B2 DMVD may be indicated by an output value associated with a probability of the dog having stage B2 DMVD that is greater than or equal to the probability at which the positive predictive value is at least 75%

(such as at least 80%, at least 85%, at least 90%, at least 95%, at least 96%, at least 97%, at least 98%, or at least 99%). Preferably, the presence of stage B2 DMVD may be indicated by an output value associated with a probability of the dog having stage B2 DMVD that is greater than or equal to the probability at which the positive predictive value is at least 95%. The probability at which the positive predictive value is at least 95% may be 0.872.

The absence of stage B2 DMVD may be indicated by an output value associated with a probability of the dog having stage B2 DMVD that is less than or equal to the probability at which the negative predictive value is at least 75% (such as at least 80%, at least 85%, at least 90%, at least 95%, at least 96%, at least 97%, at least 98%, or at least 99%). Preferably, the absence of stage B2 DMVD may be indicated by an output value associated with a probability of the dog having stage B2 DMVD that is less than or equal to the probability at which the negative predictive value is at least 95%. The probability at which the negative predictive value is at least 95% may be 0.106.

Preferably, the presence of stage B2 DMVD is indicated by an output value associated with a probability of the dog having stage B2 DMVD that is greater than or equal to the probability at which the positive predictive value is at least 75% (such as at least 80%, at least 85%, at least 90%, at least 95%, at least 96%, at least 97%, at least 98%, or at least 99%), and the absence of stage B2 DMVD is indicated by an output value associated with a probability of the dog having stage B2 DMVD that is less than or equal to the probability at which the negative predictive value is at least 75% (such as at least 80%, at least 85%, at least 90%, at least 95%, at least 96%, at least 97%, at least 98%, or at least 99%). The positive predictive value may be at least 75% and the negative predictive value may be at least 75%. The positive predictive value may be at least 80% and the negative predictive value may be at least 80%. The positive predictive value may be at least 85% and the negative predictive value may be at least 85%. The positive predictive value may be at least 90% and the negative predictive value may be at least 90%. The positive predictive value may be at least 95% and the negative predictive value may be at least 95%. The positive predictive value may be at least 96% and the negative predictive value may be at least 96%. The positive predictive value may be at least 97% and the negative predictive value may be at least 97%. The positive predictive value may be at least 98% and the negative predictive value may be at least 98%. The positive predictive value may be at least 99% and the negative predictive value may be at least 99%. Preferably, the positive predictive value is at least 95% and the negative predictive value is at least 95%.

The presence of stage B2 DMVD may be indicated by an output value associated with a probability of the dog having stage B2 DMVD of greater than or equal to than 0.6. The presence of stage B2 DMVD may, for example, be indicated by an output value associated with a probability of the dog having stage B2 DMVD of 0.7 to 1.0, such as 0.72 to 0.98, 0.74 to 0.96, 0.76 to 0.94, 0.78 to 0.92, 0.8 to 0.9, 0.82 to 0.88, or 0.84 to 0.86. The presence of stage B2 DMVD may, for example, be indicated by an output value associated with a probability of the dog having stage B2 DMVD of greater than or equal to 0.65, greater than or equal to 0.7, greater than or equal to 0.75, greater than or equal to 0.8, greater than or equal to 0.825, greater than or equal to 0.85, greater than or equal to 0.870, greater than or equal to 0.872, greater than or equal to 0.875, greater than or equal to 0.9, greater than or equal to 0.925, greater than or equal to 0.95, greater than or equal to 0.96, greater than or equal to 0.97, greater than or equal to 0.975, greater than or equal to 0.98, greater than or equal to 0.985, greater than or equal to 0.99, or greater than or equal to 0.995. The presence of stage B2 DMVD may, for instance, be indicated by an output value associated with a probability of the dog having stage B2 DMVD of greater than or equal to 0.7. The presence of stage B2 DMVD may, for instance, be indicated by an output value associated with a probability of the dog having stage B2 DMVD of greater than or equal to 0.75. The presence of stage B2 DMVD may, for instance, be indicated by an output value associated with a probability of the dog having stage B2 DMVD of greater than or equal to 0.8. Preferably, he presence of stage B2 DMVD is indicated by an output value associated with a probability of the dog having stage B2 DMVD of greater than or equal to 0.872.

The absence of stage B2 DMVD may be indicated by an output value associated with a probability of the dog having stage B2 DMVD of less than 0.995. The absence of stage B2 DMVD may, for example, be indicated by an output value associated with a probability of the dog having stage B2 DMVD of 0 to 0.8, such as 0.05 to 0.75, 0.1 to 0.7, 0.15 to 0.65, 0.2 to 0.6, 0.25 to 0.55, 0.3 to 0.5, 0.35 to 0.45. The absence of stage B2 DMVD may, for example, be indicated by an output value associated with a probability of the dog having stage B2 DMVD of less than 0.99, less than 0.985, less than 0.98, less than 0.975, less than 0.97, less than 0.96, less than 0.95, less than 0.925, less than 0.9, less than 0.875, less than 0.872, less than 0.87, less than 0.85, less than 0.825, less than 0.8, less than 0.75, less than 0.7, less than 0.65, less than 0.6, less than 0.55, less than 0.45, less than 0.4, less than 0.35, less than 0.3, less than 0.25, less than 0.2, less than 0.15, less than 0.125, less than 0.11, less than 0.106, or less than 0.1. The absence of stage B2 DMVD may, for instance, be indicated by an output value associated with a probability of the dog having stage B2 DMVD of less than 0.8. The absence of stage B2 DMVD may, for instance, be indicated by an output value associated with a probability of the dog having stage B2 DMVD of less than 0.75. The absence of stage B2 DMVD may, for instance, be indicated by an output value associated with a probability of the dog having stage B2 DMVD of less than 0.7. Preferably, the absence of stage B2 DMVD is indicated by an output value associated with a probability of the dog having stage B2 DMVD of less than 0.106.

For example, the presence of stage B2 DMVD may be indicated by an output value associated with a probability of the dog having stage B2 DMVD of greater than or equal to 0.6, 0.7, 0.75, 0.8, 0.85, 0.872, 0.9, 0.95, 0.96, 0.97, 0.98 or 0.99, and the absence of stage B2 DMVD may be indicated by an output value associated with a probability of the dog having stage B2 DMVD of less than 0.106, 0.6, 0.7, 0.75, 0.8, 0.85, 0.9, 0.95, 0.96, 0.97, 0.98 or 0.99. The presence of stage B2 DMVD may be indicated by an output value associated with a probability of the dog having stage B2 DMVD of greater than or equal to 0.6, 0.7, 0.75, 0.8, 0.85, 0.9, 0.95, 0.96, 0.97, 0.98, 0.99 or 0.872, and the absence of stage B2 DMVD may be indicated by an output value associated with a probability of the dog having stage B2 DMVD of less than 0.6, 0.7, 0.75, 0.8, 0.85, 0.9, 0.95, 0.96, 0.97, 0.98, 0.99 or 0.106 respectively. The presence of stage B2 DMVD may be indicated by an output value associated with a probability of the dog having stage B2 DMVD of greater than or equal to 0.6, 0.7, 0.75, 0.8, 0.85, 0.9, 0.95, 0.96, 0.97, 0.98 or 0.99, and the absence of stage B2 DMVD may be indicated by an output value associated with a probability of the dog having stage B2 DMVD of less than 0.6, 0.55, 0.5, 0.45, 0.4, 0.35, 0.3, 0.25, 0.2, 0.15 or 0.125. The presence of stage B2 DMVD may be indicated by an output value associated with a probability of the dog having stage B2 DMVD of greater than or equal to 0.6, 0.7, 0.75, 0.8, 0.85, 0.9, 0.95, 0.96, 0.97, 0.98 or 0.99, and the absence of stage B2 DMVD may be indicated by an output value associated with a probability of the dog having stage B2 DMVD of less than 0.6, 0.55, 0.5, 0.45, 0.4, 0.35, 0.3, 0.25, 0.2, 0.15 or 0.125 respectively. The presence of stage B2 DMVD may be indicated by an output value associated with a probability of the dog having stage B2 DMVD of greater than or equal to 0.872. The absence of stage B2 DMVD may be indicated by an output value associated with a probability of the dog having stage B2 DMVD of less than 0.106. Preferably, the presence of stage B2 DMVD is indicated by an output value associated with a probability of the dog having stage B2 DMVD of greater than or equal to 0.872, and the absence of stage B2 DMVD is indicated by an output value associated with a probability of the dog having stage B2 DMVD of less than 0.106.

The diagnosed presence or absence of stage B2 DMVD may be used to inform a clinical decision, for instance the decision to initiate treatment with a cardiac medication. For example, treatment with a cardiac medication may be initiated if the presence of stage B2 DMVD is diagnosed. The cardiac medication may, for example, be pimobendan.

Method of Training

The invention provides a method of training a model to predict stage B2 DMVD in a dog, the method comprising: (i) processing characteristic data relating to a dog using the model to output an output value, the characteristic data comprising two or more of: appetite, BCS, creatinine concentration, murmur intensity, NT-proBNP concentration, age, alanine aminotransferase (ALT) activity, breed, sex, cTnI, cough, exercise tolerance, heart rate, heart rhythm, respiratory rate, albumin concentration, alkaline phosphatase (ALKP) concentration, bilirubin concentration, blood urea nitrogen (BUN) concentration, calcium concentration, cholesterol concentration, gamma-glutamyl transferase (GGT) concentration, globulin concentration, glucose concentration, phosphate concentration, potassium concentration, symmetric dimethylarginine (SDMA) concentration, and sodium concentration; (ii) comparing the output value to a diagnosis of presence or absence of stage B2 DMVD in the dog; and (iii) adjusting the parameters of the model based on the result of the comparison. The method of training may further comprise: (iv) repeating steps (i) to (iii) one or more times, wherein the characteristic data relate to a different dog each time steps (i) to (iii) are performed.

In essence, the model is provided with characteristic data relating to a dog that has already been diagnosed with the presence or absence of stage B2 DVMD. The output value generated by the is model is compared with the known diagnosis to check for consistency. The parameters of the model are adjusted based on the result of the comparison. For example, if the output value is associated with a low probability of stage B2 DVMD, but the dog in fact has been diagnosed with the presence of stage B2 DVMD, the parameters of the model are adjusted such that re-processing the characteristic data would generate an output value more reflective of the positive diagnosis (e.g. an output value that is associated with a higher probability of stage B2 DVMD). In this way, the accuracy and reliability of the model can be improved. Repetition step (iv) provides for iterative improvement of the model using data derived from a population of dogs already diagnosed with the presence or absence of stage B2 DVMD. Comparison of the output of the model and adjustment of the parameters of the model may be performed using characteristic data associated with a plurality of dogs previously diagnosed with the presence or absence of stage B2 DVMD. Comparison of the output of the model and adjustment of the parameters of the model may be performed by minimizing a loss function used to compare the output of the model using a gradient descent process. Comparison of the output of the model may be performed using a cross-validation process where the characteristic data associated with the plurality of dogs is divided into a plurality of sub sets and each sub-set is compared to the outputs of the model separately.

The method of training discussed above may be applied when the model is derived using a machine learning process or a regression process. For example, when the model is derived using a regularised regression process, the method of training described above may be used where the penalty function of the regularised regression process is a parameter of the model that may be adjusted based on the result of the comparison. When a SVM process is used, the position of the hyperplane is a parameter of the model that may be adjusted based on the result of the comparison. When a random forest process is used, one or more of the type of characteristic data used to make a decision at each node in a tree, the threshold value of the type of characteristic data used to make a decision at each node, and the number of nodes in a tree are parameters that may be adjusted based on the result of the comparison. The hyperparameters of the process used to derive the model may be a parameter adjusted based on the result of the comparison.

Dogs

The method of training a model to predict stage B2 DMVD in a dog comprises comparing the output value of step (i) to a diagnosis of presence or absence of stage B2 DMVD in the dog to which the characteristic data relate. In other words, it is already known whether or not the dog to which the characteristic data relates has stage B2 DMVD. The diagnosis of presence or absence of stage B2 DMVD may be based on echocardiographic examination. For example, echocardiography may be used to determine the left atrial to aortic root ratio (LA:Ao) and/or left ventricular internal diameter at end diastole normalised to bodyweight (kg) (LVIDDN). Stage B2 DMVD may be identified as present when LA:Ao is greater than or equal to 1.6 and LVIDDN is greater than or equal to 1.7. Stage B2 DMVD may be identified as absent when LA:Ao is less than 1.6 and/or LVIDDN is less than to 1.7.

The dog to which the characteristic data relate may be at least 1 (such as at least two, at least three, at least 4, at least 5, at least 6, at least 7, at least 8, at least 9 or at least 10) years old. Preferably, the dog to which the characteristic data relates may be at least 6 years old.

The dog to which the characteristic data relate may weigh at least 1 kg (such as at least 2 kg, at least 5 kg, at least 10 kg, at least 15 kg, at least 20 kg, at least 25 kg, or at least 30 kg). The dog to which the characteristic data relate may weigh between 1 kg and 70 kg, such as between 2 kg and 65 kg, between 5 kg and 60 kg, between 10 kg and 55 kg, between 15 kg and 50 kg, between 20 kg and 45 kg, between 30 kg and 40 kg, or between 30 kg and 35 kg. Preferably, the dog to which the characteristic data relates weighs between 2 kg and 25 kg.

Preferably, the dog to which the characteristic data relate has a left apical systolic murmur with a point of maximum intensity over the mitral valve. The dog to which the characteristic data relate preferably has no radiographic, historical or physical examination findings consistent with congestive heart failure. Preferably, the dog to which the characteristic data relate was not receiving treatment with a loop diuretic at the time of data collection. Preferably, the dog to which the characteristic data relate was not receiving treatment with pimobendan at the time of data collection. Preferably, the dog to which the characteristic data relates does not have comorbidities that would be expected to interfere with echocardiographic measurements or bio-marker concentrations.

Dogs are further described in detail above in connection with a method of screening for stage B2 DMVD in a dog. Any of the aspects described in connection with a method of screening for stage B2 DMVD in a dog may apply to the method of training a model to predict stage B2 DMVD in a dog.

Characteristic Data, Models and Output Values

Characteristic data, models and output values are described in detail above in connection with a method of screening for stage B2 DMVD in a dog. Any of the aspects described in connection with a method of screening for stage B2 DMVD in a dog may apply to the method of training a model to predict stage B2 DMVD in a dog.

Adjusting the Parameters

The parameters of the model may be adjusted by adjusting the weighting afforded to one or more of the characteristic data. For example, in a model derived using a regression process, the weighting associated with one or more of the characteristic data in the derived function may be changed during the adjustment. In a model derived using a SVM process, the position of the hyperplane used to classify input vectors associated with characteristic data may be modified. In a model derived using a random forest process, one or more of the types of characteristic data, the number of decision trees, the number of nodes of one or more of the decision trees and the threshold applied by any one of the nodes of the decision trees may be adjusted.

Computer Program and System

Methods and processes described herein can be embodied as code (e.g., software code) and/or data. Such code and data can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium. In certain embodiments, one or more of the steps of the methods and processes described herein can be performed by a processor (e.g., a processor of a computer system or data storage system). It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals.

Figure 7:
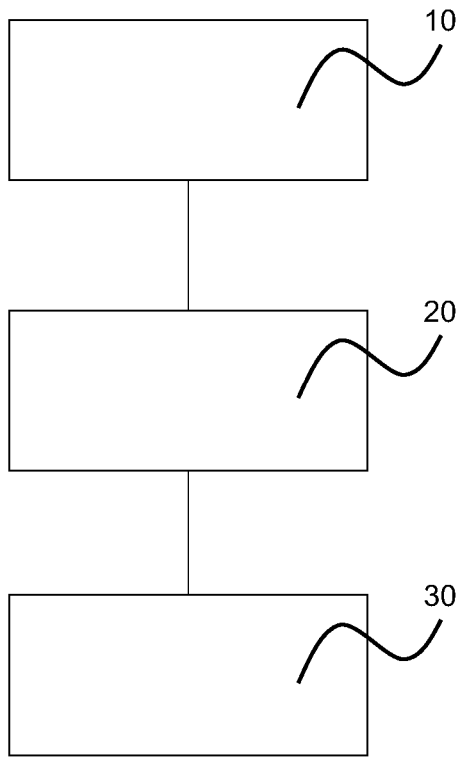
FIG. 7: A schematic example of a system for diagnosing stage B2 DMVD in dogs.

The system may comprise an input device 10 configured to receive the characteristic data relating to a dog, a model 20 configured to receive the characteristic data an generate an output value and an output device 30 configured to output the output value generated by the model. A schematic example of a system is shown in FIG. 7. Each component of the system may be at a single location. Alternatively, at least one of the components may be at a different location to the other components. Data may be sent and received between each of the components. For example, the input device may be located at a first location such a veterinary practice. The model may be located at a second location. On receipt of the characteristic data, the input device may send the characteristic data to the model at the second location. The input device may perform a conversion on the characteristic data prior to sending the characteristic data, such as a compression process. The model may receive the characteristic data, generate an output value and send the output value to the output device which may be located at the first location.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a peptide" includes "peptides", reference to "a nanoparticle" includes two or more such nanoparticles, and the like.

All publications, patents and patent applications cited herein, whether supra or infra, are hereby incorporated by reference in their entirety. The following Examples illustrate the invention.

Example 1

Methods

The study was prospective and cross sectional in design. Recruitment was international, with data captured at 17 centres in Germany, 25 in the United Kingdom and 16 in the United States of America (USA). Cases were recruited to the study during the period January 2018 to June 2019. Patient examinations were conducted by veterinary cardiologists with at least one of the following qualifications: a diploma of the cardiology subspecialty of the European College of Veterinary Internal Medicine (ECVIM-CA) or American College of Veterinary Internal Medicine (ACVIM); Royal College of Veterinary Surgeons (RCVS) cardiology diploma; RCVS cardiology certificate; membership of the Collegium Cardiologicum (CC); or membership of the working cardiology group of the Deutsche Gesellschaft für Kleintiermedizin-Deutsche Veterinärmedizinische Gesellschaft (DGK-DVG). The participation of residents in training was permitted if they were under the direct supervision of a suitably qualified cardiologist. The collection and storage of patient data were performed with owner consent and the approval of the Ethics and Welfare Committee of the Royal Veterinary College (URN: 2017 1749-3).

Case Selection

The study population consisted of client-owned dogs that were already undergoing diagnostic evaluation of their heart disease. Dogs were considered eligible for inclusion if they had received a diagnosis of DMVD by a veterinary cardiologist on the basis of an echocardiographic examination. This was defined as visible prolapse or thickening of the mitral valve and associated apparatus, in combination with mitral regurgitation on color Doppler examination. Dogs were required to be at least 6 years old, weigh between 2 and 25 kg and have a left apical systolic murmur with a point of maximum intensity over the mitral valve. Dogs were excluded from the study population if they had radiographic, historical or physical examination findings consistent with CHF or if they were already receiving treatment with a loop diuretic. Comorbidities that would be expected to interfere with echocardiographic measurements or biomarker concentrations were considered additional reasons for exclusion.

Populations Evaluated

From amongst the whole "complete" population, a "clean" population was created to remove the influence of potential confounders from analyses. Patients violating inclusion criteria, such as those with azotaemia, hypercalcaemia, endocrinopathies or moderate to marked elevations in alanine aminotransferase (ALT)[26] were excluded from this refined population, as well as patients whose samples had taken longer than 72 hours to arrive at the reference laboratory. Dogs receiving treatment with pimobendan were also excluded to eliminate the drug's reported effect on echocardiographic dimensions.[7] The data from patients removed at this stage was retained and used to form an "excluded" population for use in a sub-analysis.

Clinical Evaluation

Data were captured by veterinary cardiologists at the point of examination. The presence of a cough, as well as changes in appetite and exercise tolerance over a 6-month period were noted. Heart rate and respiratory rate were measured and the predominant heart rhythm throughout auscultation was classified as sinus rhythm, sinus arrhythmia or "other". Murmur intensity was initially attributed a value of I-VI using the Levine scale.[27] For the purposes of analysis this was reclassified to reduce complexity. Grade I and II murmurs were labelled as soft, grade III as moderate, grade IV as loud and grades V and VI as thrilling.[14] Body condition (BCS) was scored using the American Animal Hospital Association's 9 point scale.[28] Echocardiography was performed on all dogs and standard right parasternal views were obtained. Left atrial to aortic root ratio was recorded from a short-axis, 2D view in early ventricular diastole.[29] The left ventricular internal diameter in diastole (LVIDD) was recorded from a short-axis, M-mode view at the level of the chordae tendinae.[30] LVIDD was normalised to bodyweight (LVIDDN) using the formula: LVIDDN=LVIDD (cm)/Weight$^{0.294}$(kg).[31] Consistent with guidelines produced by the ACVIM, patients were considered to be in stage B2 when LA:Ao≥1.6 and LVIDDN≥1.7.[4] Dogs that did not meet both of these criteria were classified as stage B1. Where available, vertebral heart score was recorded for use in a sub-analysis.[32,33]

A venous blood sample was taken from all dogs in order to obtain a serum biochemical analysis and cardiac biomarker concentrations. Processed aliquots were sent on ice to a research laboratory in Germany or the USA depending on the point of origin of the sample (IDEXX BioResearch, Ludwigsburg, Germany; IDEXX BioAnalytics, West Sacramento, California, USA). Plasma NT-proBNP concentrations (second generation ELISA: Canine Cardiopet® proBNP.) and serum biochemistry profiles were produced at the time of receipt. Serum samples for measurements of cTnI (2-site immunoenzymatic sandwich assay: Beckman Access 2 troponin assay) were stored at −80° C. and batch processed once recruitment had been completed. Results that fell below the detection limits of the assay were assigned the value of the lower limit.[9,23]

Analytical Methods

Analyses were performed using commercially available software and open source freeware (Python Software Foundation. Python Language Reference, version 3.7; R 1.2.5019, R Foundation for Statistical Computing, Vienna, Austria; SPSS version 26.0 for Macintosh, released 2018, SPSS Inc. San Diego, USA). Statistical significance was set as P<0.05. Continuous data are reported as the median (25$^{th}$ percentile, 75$^{th}$ percentile) and categorical variables are presented as the proportion (frequency). The normality of continuous variables was assessed by visually inspecting histograms. Variables that displayed a marked right skew were logarithmically transformed or categorised into quartiles if transformation did not result in a Gaussian-like distribution. Collinearity between continuous variables was considered if Spearman's rho exceeded 0.7. Categorical variables with small group sizes were reclassified into broader levels prior to inclusion in analyses.

Identification of Factors Associated with the Presence of Stage B2 DMVD

Within the "clean" population binary logistic regression was used to identify risk factors associated with having stage B2 disease. Cases were dichotomised according to whether or not they were in stage B2 and clinical data and blood test concentrations were entered as explanatory variables.[4] Laboratory location was tested as a potential confounder. Univariable restricted cubic spline models were used to assess the assumption of linearity with the logit.[34] When this was violated, continuous variables were categorised into quartiles for all subsequent analyses.[35] Variables that displayed an association with the outcome at a univariable level (P<0.2) were included in an explanatory multivariable analysis and backwards stepwise elimination was used to select a preliminary main effects model using likelihood ratio tests.[36] Variables that had been excluded by univariable testing were individually entered into the main effects model and retained if they induced a substantial change in the coefficients (>20%) indicative of a confounding effect.[36] Two-way interaction terms were tested for plausible combinations of variables and included in the multivariable model if they displayed a significant association with disease stage.[36] Post-hoc estimated marginal means were calculated for all categorical variables that remained in the final model.

Results are reported as coefficients (β) and odds ratios (OR) with 95% confidence intervals (CI).

A Comparison of Discriminatory Ability in Alternate Settings

Model performance was assessed by plotting a receiver operating characteristic (ROC) curve using predicted probabilities and calculating the area under the curve (AUC) with 95% confidence intervals. In order to evaluate the degree to which comorbidities, sample handling or pimobendan administration affected discriminatory ability, the coefficients for the explanatory multivariable model were applied to data from the "complete" and "excluded" populations. AUCs for the clean, complete and excluded populations were compared using a DeLong test.[37] The discriminatory ability of the explanatory multivariable model was additionally compared to other methods that could be used to identify stage B2 DMVD. Disease stage was regressed on NT-proBNP alone and vertebral heart score alone in separate univariable logistic regression models, from which AUC was calculated.

Evaluating the Predictive Performance of Classifiers Trained to Identify StageStage B2 Disease A series of diagnostic classifiers were developed to evaluate how readily preclinical disease status could be predicted. The models tested were logistic regression, Ridge regression,[38] Support Vector Machines (SVM),[39] Random Forest[40] and the Gradient Boosting Machine (GBM) XGBoost.[41] The clean data were partitioned, with 80% used for training and the remaining 20% kept separate as a holdout testing population. Rows containing missing data were not included in this split. Transformation functions for data pre-processing were developed on the training set and applied to test data at the point of prediction. For all models except logistic regression and decision tree algorithms, continuous variables were scaled using the formula $(x_i-\bar{x})/\sigma(x)$. Categorical variables were dummy encoded (k–1) for logistic regression and one hot encoded for other algorithm types (k). If applicable, an optimal combination of hyperparameters was selected using a grid search of the hyperparameter space, with each combination tested in an internal 5-fold cross validation loop. For the development of the predictive logistic regression model, features were selected by backwards stepwise elimination using the likelihood ratio test. A significance level of 0.05 was used to select the most parsimonious model. Variability in predictions was estimated by fitting tuned models to 500 bootstraps that had been sampled randomly from the training set with replacement[42] and then calculating the standard deviation of results.[43] Models were fitted to the test set to generate predictions of outcome status. Overall accuracy was assessed using the Brier score, which represents the mean squared error between predicted probabilities and the outcome.[44] The ability to discriminate between stages B1 and B2 was evaluated using the AUC (95% CI) and the agreement between predicted probabilities and the prevalence in the testing population was assessed using the intercept (calibration in the large) and slope of a calibration curve.[44-46] Plots of variable importance were produced to assess agreement between models and examine the workings of black box algorithms such as SVM, Random Forest and GBM.

Results

The complete study population consisted of 1887 dogs with preclinical DMVD. Six hundred and forty-two dogs were excluded from the complete population on the basis of their age (n=56, 2.75%), bodyweight (n=10, 0.53%), comorbidities (n=126, 6.68%), pimobendan medication (n=361, 19.13%) or due to errors with sample handling (n=162, 8.59%). Of the 361 dogs receiving treatment with pimobendan, 56.51% (n=204) met the criteria for stage B2 disease. After exclusion of these dogs a clean population was produced which comprised 1245 dogs (FIG. 1).

Amongst the clean population, 27.1% (n=337) of dogs were classified as having stage B2 disease. The most common breed evaluated was the Cavalier King Charles Spaniel (n=292, 27.07%), followed by Chihuahuas (n=84, 6.74%), Jack Russell Terriers (n=56, 4.50%), Shih Tzus (n=43, 3.45%) and Cocker Spaniels (n=43, 3.45%). The median age was 10.00 years (LQ, 8.08; UQ, 11.63) and the group was formed of more male (n=718, 57.67%) than female dogs (n=527, 42.33%). Thirty one percent of dogs (n=387) reported clinical signs, of which a cough was the most common complaint (n=299, 24.02%). Only 14.1% dogs (n=175) had undergone thoracic imaging and had a VHS reported, with the median score being 11.00 (LQ, 10.50; UQ, 11.50). Additional descriptive statistics are reported in Tables 1, 2 and Supplementary Tables 1, 2.

Identification of Factors Associated With the Presence of Stage B2 DMVD

Figure 6:
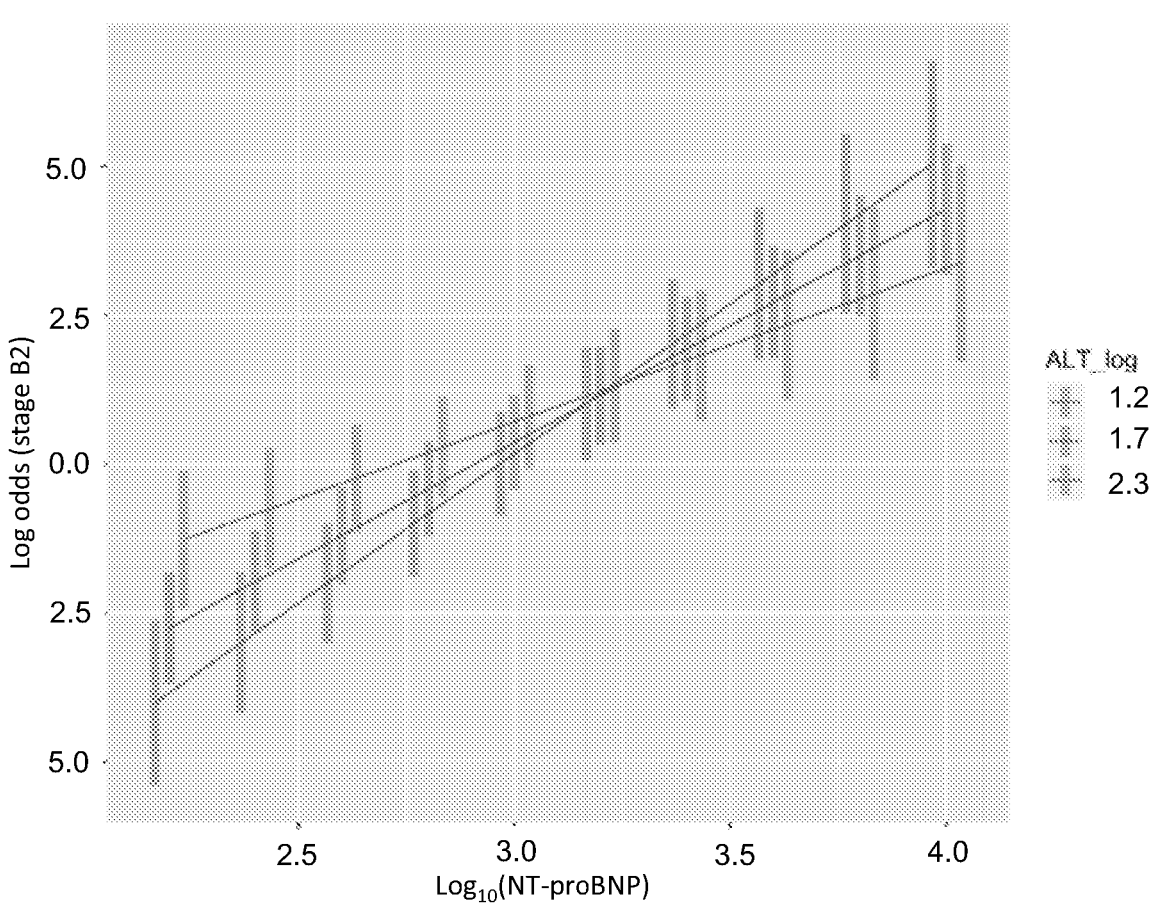
FIG. 6: Slopes for the interaction between ALT and NT-proBNP. NT-proBNP is plotted against the log odds of having stage B2 disease at different levels of ALT.

In univariable testing, 18 variables demonstrated an association with disease stage. In the multivariable analysis, the following variables were identified as independent risk factors: age, ALT activity, appetite, BCS, creatinine concentration, murmur intensity and NT-proBNP concentration (Table 3). A reduction in appetite and lower body condition score were associated with greater odds of being in stage B2 and post hoc testing of BCS demonstrated that this was true when underweight scores (BCS≤3) were compared to almost all other values (Table 4b). Estimated marginal means for murmur intensity showed that the likelihood of being in stage B2 was greater when murmurs were more audible, with the comparison between loud and thrilling murmurs being the only pairwise combination that did not significantly differ (Table 4c). Patient age was also associated with the outcome, with dogs between 8 and 10 years old at greatest risk. In dogs older than 10, the likelihood of being stage B2 was significantly lower (Table 4a). Increasing serum creatinine concentrations were associated with a small reduction in the odds of being in stage B2 (β, –0.02; OR 0.98, CI 0.97 — .99; P<0.001). In contrast, the likelihood was greater at higher values of $\log_{10}$(NT-proBNP) and $\log_{10}$(ALT), when these variables were modelled as main effects. ALT and NT-proBNP negatively interacted, meaning that the association between $\log_{10}$(NT-proBNP) and the outcome was not as strong at higher values of $\log_{10}$(ALT) (FIG. 6).

A Comparison of Discriminatory Ability in Alternate Settings

Figure 2:
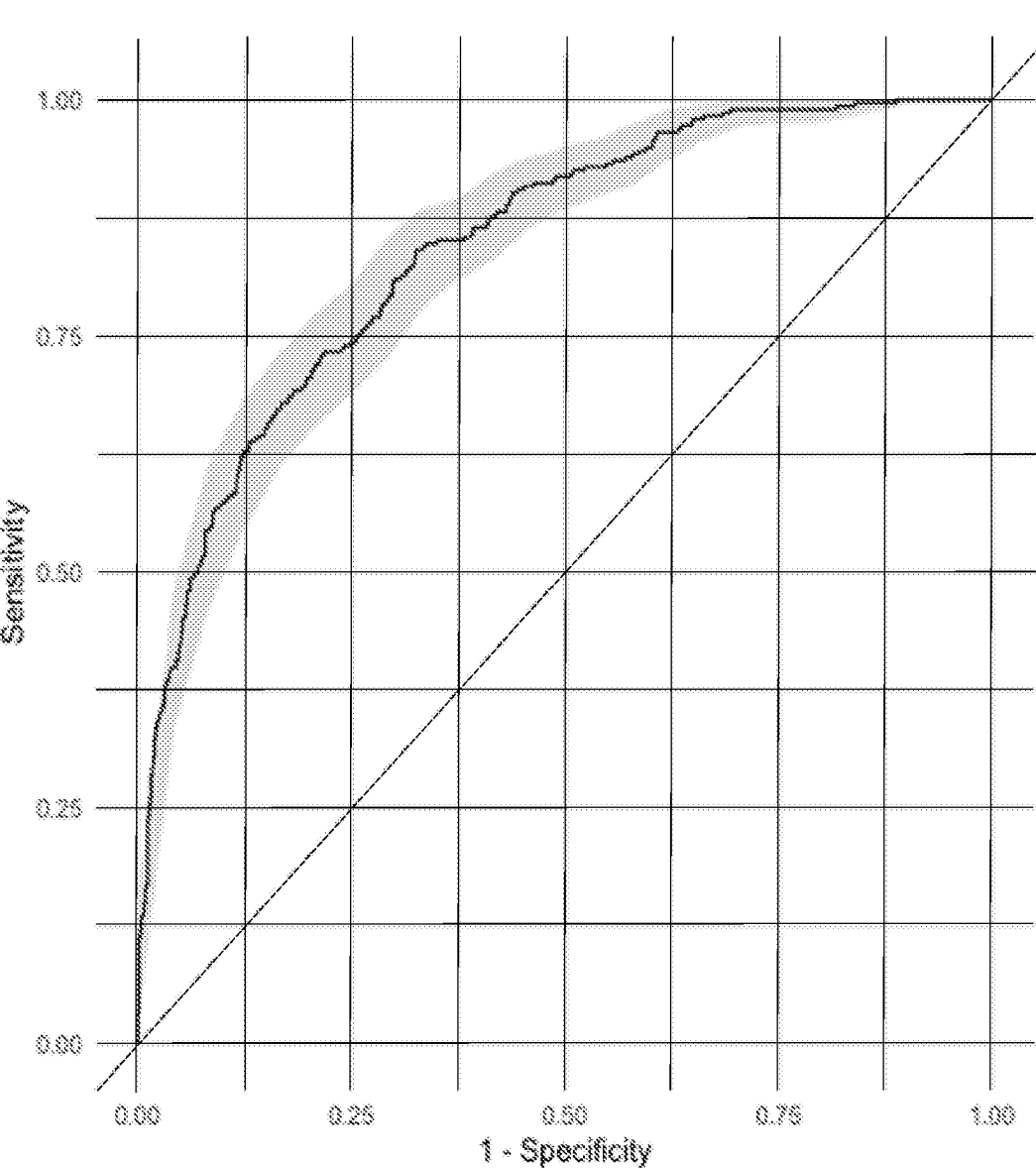
FIG. 2: A receiver operating characteristic curve for the explanatory multivariable logistic regression analysis of risk factors associated with having stage B2 disease. 95% confidence intervals are represented by the blue area around the receiver operating curve. Area under the curve: 0.84 (0.82-0.87).
Figure 3:
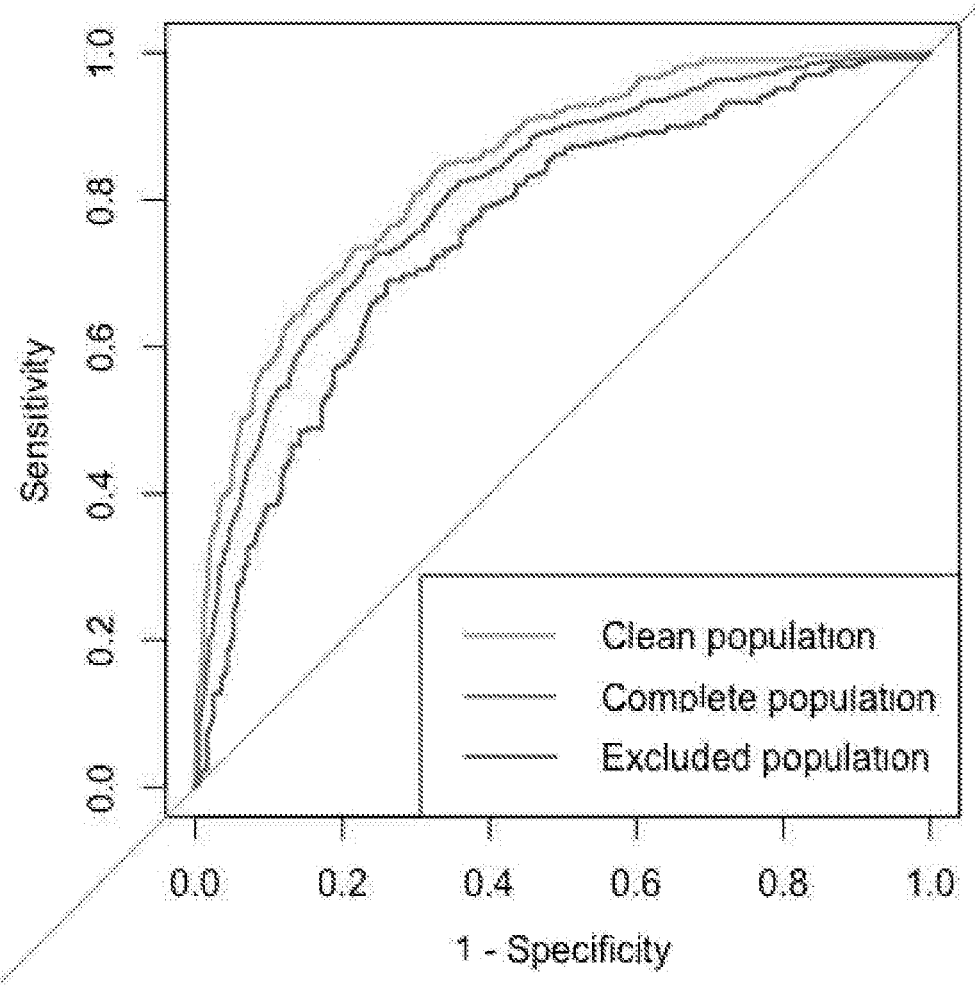
FIGS. 3 and 4 provide a comparison of receiver operating characteristic curves
Figure 4:
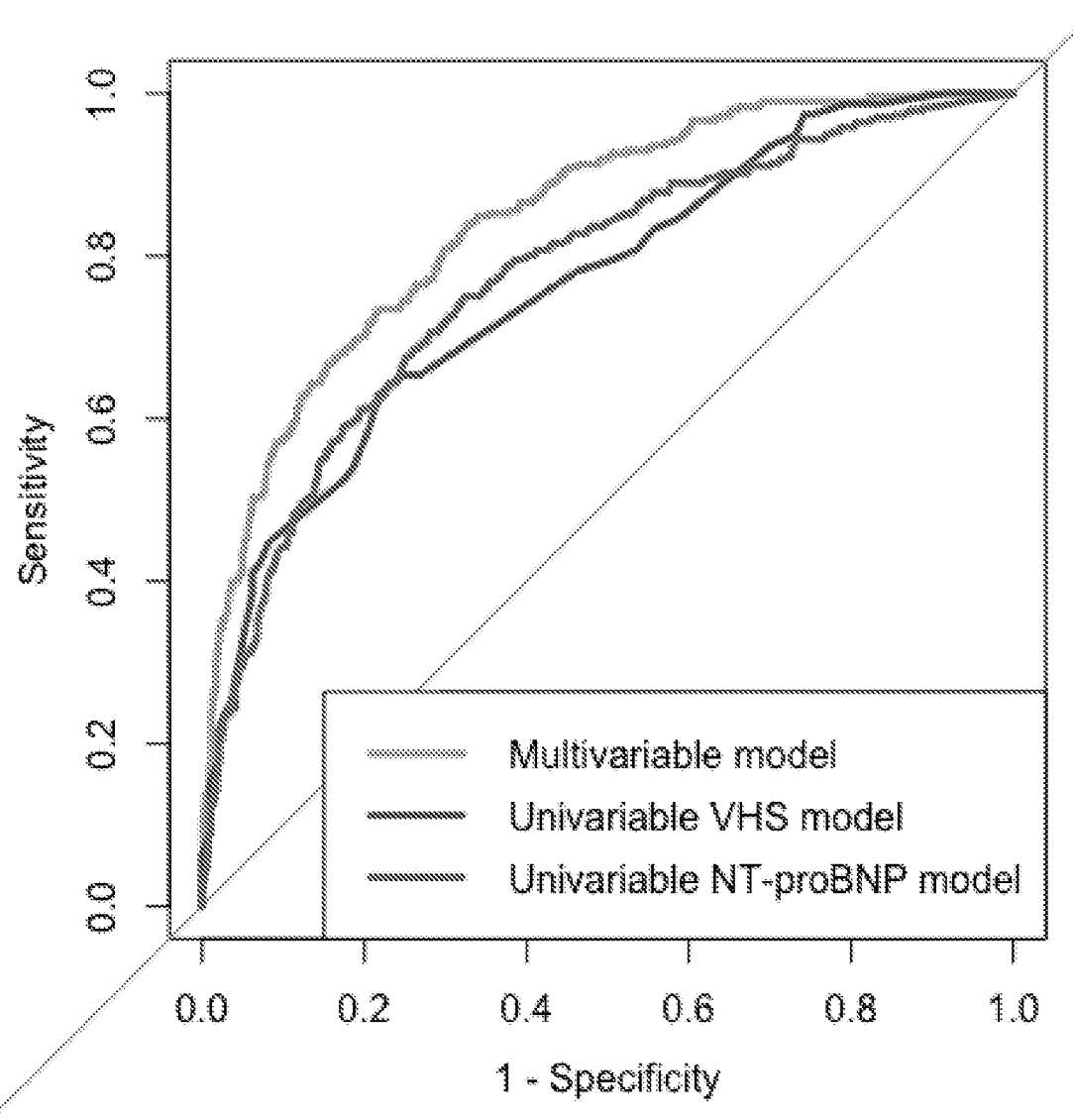

The final explanatory multivariable model containing all significant predictors was shown to discriminate well between preclinical disease stages (AUC, 0.84; 95% CI, 0.82 -0.87; Nagelkerke R2, 0.42) (FIG. 2). When applied to the complete population, discriminatory performance decreased by a small amount (AUC, 0.81; 95% CI, 0.79-0.83; P=0.048) (FIG. 3). In the excluded population; comprised of data that had not been used for model derivation, performance was fair but significantly lower than when tested in more optimal conditions (AUC, 0.76; 95% CI, 0.72-0.80; P<0.001)[36] Univariable models produced for NT-proBNP and VHS found that these variables were positively associated with the odds of being in stage B2 (NT-proBNP: β, 3.65; OR 38.45, 95% CI 23.14-65.42, P<0.001, Nagelkerke $R^2$ 0.26. VHS: β, 1.28; OR 3.81, 95% CI 2.33-5.96, P<0.001, Nagelkerke $R^2$ 0.29). Values of AUC were lower and had wider confidence intervals than the multivariable explanatory model, indicating that model performance decreased when using these alternate methods of diagnosis (NT-proBNP: AUC, 0.77; 95% CI, 0.74-0.80. VHS: AUC, 0.76; 95% CI, 0.69-0.83) (FIG. 4). This difference in AUC indicated that both models based on a single parameter performed significantly worse than the explanatory multivariable model (NT-proBNP: P<0.001. VHS: P=0.032).

Figure 5:
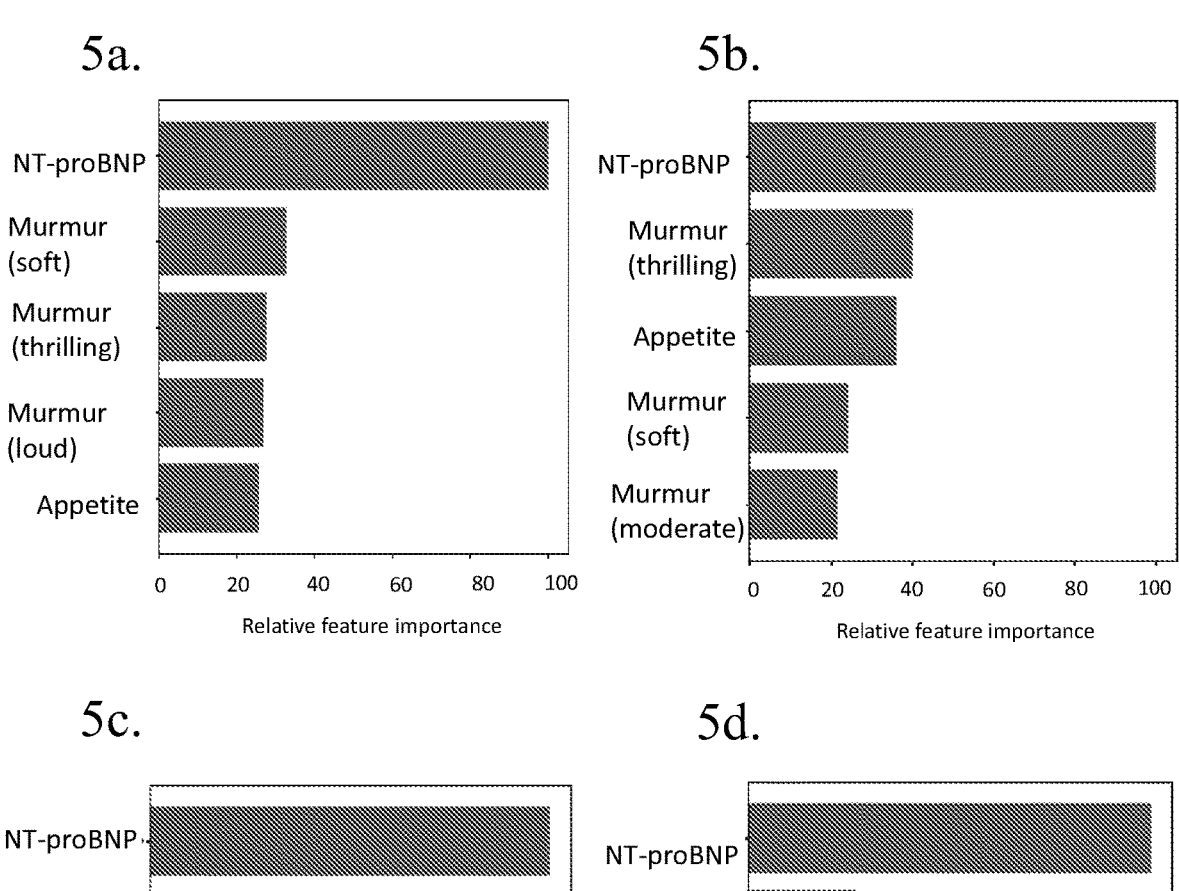
FIG. 5: Variable importance plots displaying the 5 most important variables for the following classifiers: a) ridge regression, b) Support Vector Machine with a linear kernel, c) Random Forest and d) GBM. Variable importance is presented relative to the most important predictor in each model. Scores for ridge regression and the support vector machine with a linear kernel are the coefficients for each variable. Scores for Random Forest and GBM are the mean Shapely value for each variable. BCS, body condition score; BUN, blood urea nitrogen; GBM, gradient boosting machine; NT-proBNP, N-terminal propeptide of B-type natriuretic peptide
Figure 5:
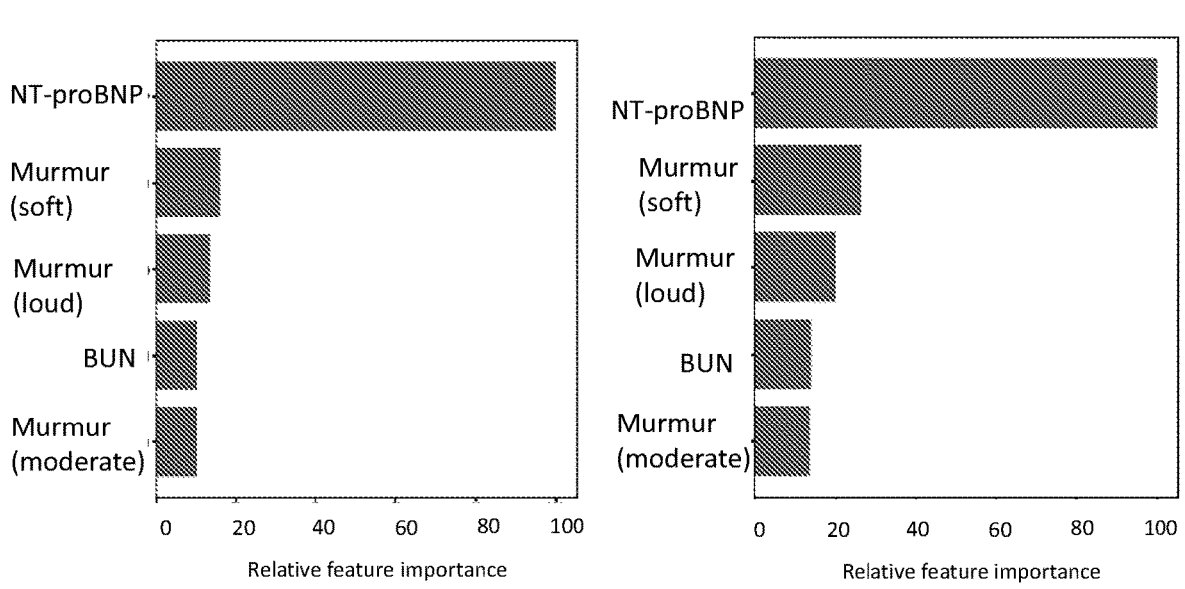

Evaluating the Predictive Accuracy of Classifiers Trained to Identify StageStage B2 Disease When evaluating the AUC for predictions on the test data, model performance was relatively consistent across classifiers with a mean value of 0.87, indicating that all models generalised well to new data. Calibration in the large was positive for all models, which indicates a small propensity for models to overestimate predicted probability as a whole.[44] Further performance metrics are summarised in Table 5. NT-proBNP and murmur grade were consistently found amongst the most important predictors, with NT-proBNP ranking first in all models tested (FIG. 5). These variables were featured in the predictive logistic regression model alongside appetite, creatinine and BCS (Table 6). This predictive logistic regression model, with 5 features selected through backwards stepwise elimination, performed similarly to the more complex explanatory model containing all variables (AUC test, 0.86; 95% CI, 0.81-0.91), indicating that appetite, BCS, serum creatinine concentration, murmur intensity and NT-proBNP concentration explained the majority of variation in the data. The outcome produced by this predictive model represents the predicted probability that a patient has stage B2 disease. As the presentation of results affects how well a model is implemented,[47] positive and negative predictive values are provided to guide interpretation (Table 7).

Discussion

Our study found that clinical observations and cardiac biomarker concentrations could be used to predict the risk of a dog with DMVD being in stage B2. Using information obtained from a single examination of 1887 patients, a series of classifiers were able to predict preclinical disease stage with good discrimination (AUC mean, 0.87) and calibration.[36]

Previous research has recognised that there is a need to diversify the range of diagnostic options available in DMVD because of differences in patient circumstances0.9,18,24,48 Informed decision making in the preclinical phase of disease is of particular importance to maximise the number of dogs that are managed correctly. The predictive models defined in the present study have the potential to act as an initial screening test, quantifying the risk of having stage B2 disease. High risk scores could be used to select patients that would benefit from further investigation and low risk scores may identify dogs that are more likely to be stage B1. In this study, a model derived using multivariable logistic regression had similar predictive performance to other more complex classifiers that were tested. This is potentially advantageous, as it requires fewer parameters to make a prediction, thus reducing cost which could be a barrier to uptake.[44] The model was internally validated against a holdout set of 20% of the cohort and, on the basis of this analysis, it was possible to infer that it would perform well in the general population of dogs in primary-care practice. An important next step is to assess the model's accuracy in the exact set of circumstances in which it is intended for use.[44,49]

All predictive models ranked NT-proBNP as the most important variable when differentiating between stages B1 and B2. In the explanatory analysis, the likelihood of having stage B2 disease increased as NT-proBNP concentration increased, supporting previous associations with disease severity.[18,19,50,51] When comparing the multivariable explanatory model with one containing NT-proBNP alone, it was apparent that including other risk factors alongside the biomarker increased discriminatory performance, reducing the number of misclassified cases. As well as capturing additional sources of variation in the outcome measure, this approach may have improved performance by controlling for variability in the biomarker itself. In dogs, NT-proBNP concentrations are affected by comorbidities and serial measurements within the same individual display biological variability.[52-54] Including more than one marker of disease severity may therefore improve the quality of predictions in cases with anomalous biomarker concentrations. The findings of this explanatory analysis are similar to previous studies, indicating that NT-proBNP is more informative when interpreted alongside other factors.[9,23,24] This results in improved accuracy when staging preclinical disease.

In addition to NT-proBNP, several other risk factors were identified. Murmur intensity, another important predictive variable, has been previously associated with preclinical disease severity.[11,14] In agreement, our study's explanatory analysis found that the likelihood of being in stage B2 increased with murmur grade, with dogs having loud or thrilling murmurs at the greatest risk. Compared with the other parameters included in this analysis, murmur intensity is one of the more subjective measurements. Cardiac auscultation is subject to inter- and intra-observer variability, which is potentially limiting considering the apparent importance of this variable.[11,55] Previous research has shown that the use of simpler schemes improves agreement so, for the purpose of this study, audibility was graded using the 4 level system proposed by Ljungvall et al (2014).[14,56] It is still important to note that all dogs were examined by veterinary cardiologists using a standardised protocol. Further research is required to assess whether sampling in a different setting impacts the accuracy of predictions.

Having a reduced appetite was found to increase the likelihood of being stage B2. In DMVD, loss of appetite is considered a negative prognostic indicator and dogs that go on to develop CHF may experience reductions in body weight.[5,7,48] Though weight was not examined in the present analyses, poor body condition was associated with increased risk of being B2. A syndrome of anorexia-cachexia is recognised in human patients with functional heart failure.[57,58] In dogs, cachexia may develop prior to the onset of CHF, resulting in changes that can be detected as clinical signs. Subsequent losses in muscle mass may also influence serum creatinine concentrations. In this study, a negative association was observed between creatinine and the odds of being stage B2, supporting this hypothesis. Creatinine was retained in multivariable models in favour of SDMA, indicating that it described additional variation outside of glomerular filtration rate (GFR). GFR itself may be expected to display an association with the severity of preclinical disease as increases in circulating fluid volume have been shown to induce a more rapid rate of creatinine clearance.[59-63] Adjusting for creatinine in a model containing NT-proBNP is potentially advantageous as GFR is a known confounder of the biomarker's concentrations.

Though age and ALT were associated with the likelihood of being stage B2, both variables were not retained in the predictive logistic regression model derived from a smaller subset of data, which raises questions about the strength of these associations. In explanatory analyses, the greatest risk was observed when dogs were between 8 and 10 years old. After this, ageing patients were less likely to have stage B2 disease. There is evidence that the propensity to remodel is altered in the ageing heart, however this has not been studied in DMVD.[64] It is possible that pro-fibrotic changes in myocardial composition impact the development of eccentric hypertrophy.[65] Alternatively, these findings may reflect differences in the phenotypes contained within each age group. Early onset DMVD, as noted in some breeds, may be accompanied by a more rapid rate of disease progression.[3,9] In humans, age is considered when defining diagnostic thresholds for NT-proBNP and research has shown that this adds additional value to analyses that already account for creatinine.[66] Thus, including age in models may correct for potential confounding in dogs.

ALT was positively associated with the likelihood of being stage B2 in the explanatory analysis. The hepatic vasculature is sensitive to changes in central venous pressure and elevations in ALT can occur secondary to cardiovascular disease as a result of congestion or reduced perfusion.[67,68] ALT was shown to modify the strength of the relationship between NT-proBNP and disease stage, though the exact relevance of this finding in DMVD is not clear. It is possible that at high ALT concentrations, NT-proBNP is partially elevated as a consequence of liver disease, producing a weaker association with DMVD severity.[69,70]

The study benefited from the large number of patients examined. This facilitated robust analyses, particularly when developing a predictive model for clinical use. When training any model, it is possible that the algorithm will over-fit non-meaningful noise in the data, reducing generalisability.[71] In this study, there were enough patients to form separate training and testing cohorts. This partitioning technique simulates performance in new conditions, as trained models are applied to a set of data that they have not previously encountered. Several algorithms were compared and there was good agreement in model fit, internal generalisability and the variables of greatest importance. All models identified NT-proBNP as the most highly ranked variable, which supports research that describes its potential relevance in preclinical DMVD.[9,18,19]

The data were substantial enough to evaluate several machine learning algorithms and present them in comparison with more conventional regression-based models. Machine learning has potential applications in medicine as algorithms can describe complex, non-linear relationships between variables.[72] Using machine learning to distinguish between stages B1 and B2 did not produce a marked performance advantage in this study, indicating that parametric, linear methods sufficiently captured the data structure.[73] In this instance, the logistic regression model may be considered more clinically useful as it provides a parsimonious and interpretable set of specifications. Though machine learning shows promise in veterinary medicine,[74, 75] the results of this study highlight that it does not always provide an optimal solution. Model selection is equally dependent upon the data and the model's intended use.

Prospectively sampling a large number of dogs captured data from other diagnostic tests conducted at the time of examination. This was sufficient to allow a sub-analysis of VHS; an alternative method of identifying cardiomegaly. In comparison with single tests like VHS or NT-proBNP, a multi-parameter approach was more accurate, which concurs with the results of other studies.[9,23,24,48] Though differences in clinical usefulness were not precisely measured, integrating routine data with a single blood test allows the user to avoid risk that comes with radiation exposure or chemical restraint.[76]

Conclusion

In conclusion, this study shows that data obtained from multiple aspects of a patient's examination, specifically: appetite, BCS, creatinine, murmur intensity and NT-proBNP can be used to predict the likelihood that a dog has stage B2 DMVD. This has the potential as a screening test and may provide an informed way to allocate client and practice resources. Ultimately, the correct application of a clinical prediction model may improve outcomes for dogs with preclinical DMVD.

Tables

TABLE 1

Patient characteristics for dogs with stage B1 or stage B2 degenerative mitral valve disease. Descriptive statistics are reported for the clean dataset. BCS, body condition score; CKCS, Cavalier King Charles Spaniel; ACEi, angiotensin converting enzyme inhibitor. A hyphen (-) is used to indicate that there were no missing data for this variable.

| Variable | | Population | | | |
|---|---|---|---|---|---|
| | | B1 (n = 908) | Missing | B2 (n = 337) | Missing |
| Age (years) | | 10.00 (8.00, 11.67) | 0.11% (1) | 10.00 (8.50, 11.35) | 0.30% (1) |
| BCS | ≤3 | 1.76% (16) | 0.44% (4) | 3.86% (13) | 0.59% (2) |
| | 4 | 16.63% (151) | | 14.24% (48) | |
| | 5 | 41.63% (378) | | 43.32% (146) | |

TABLE 1-continued

Patient characteristics for dogs with stage B1 or stage B2 degenerative mitral
valve disease. Descriptive statistics are reported for the clean dataset. BCS, body
condition score; CKCS, Cavalier King Charles Spaniel; ACEi, angiotensin
converting enzyme inhibitor. A hyphen (-) is used to indicate that there were no
missing data for this variable.

| Variable | | B1 (n = 908) | Missing | B2 (n = 337) | Missing |
|---|---|---|---|---|---|
| | | | Population | | |
| | 6 | 22.36% (203) | | 28.49% (96) | |
| | 7 | 12.78% (116) | | 6.82 (23) | |
| | ≥8 | 4.41% (40) | | 2.67% (9) | |
| Breed | CKCS | 22.69% (206) | - | 25.52% (86) | - |
| Cardiac medications | ACEi | 3.41% (31) | - | 3.56% (12) | - |
| | Spironolactone | 0.44% (4) | - | 1.48% (5) | - |
| Sex | Female entire | 4.07% (37) | - | 2.67% (9) | - |
| | Female neutered | 39.10% (355) | | 37.39% (126) | |
| | Male entire | 12.11% (110) | | 11.28% (38) | |
| | Male neutered | 44.71% (406) | | 48.66% (164) | |
| Weight (kg) | | 9.30 (6.80, 12.60) | - | 8.70 (6.50, 11.30) | - |

TABLE 2

Clinicopathological data for dogs with stage B1 or stage B2 degenerative mitral
valve disease. Descriptive statistics are reported for the clean dataset. cTnI, cardiac
troponin I; NT-proBNP, N-terminal propeptide of B-type natriuretic peptide; ALKP,
alkaline phosphatase; ALT, alanine aminotransferase; BUN, blood urea nitrogen; GGT,
gamma-glutamyl transferase; SDMA, symmetric dimethylarginine; TS, total solids; VHS,
vertebral heart score. A hyphen (-) is used to indicate that there were no missing data for
this variable.

| Variable (Laboratory Reference Interval) | | B1 (n = 908) | Missing | B2 (n = 337) | Missing |
|---|---|---|---|---|---|
| | | | Population | | |
| Appetite | Decreased | 0.66% (6) | - | 2.67% (9) | 0.30% (1) |
| Cardiac biomarkers | cTnI (ng/ml) | 0.05 (0.03, 0.08) | 1.43% (13) | 0.06 (0.04, 0.10) | 1.78% (6) |
| | NT-proBNP (pmol/L) | 589.50 (373.50, 877.25) | - | 1188.00 (774.00, 2000.00) | - |
| Cough | Yes | 20.15% (183) | - | 34.4% (116) | - |
| Exercise tolerance | Decreased | 9.58% (87) | - | 15.43% (52) | - |
| Heart rate | | 120.00 (104.00, 132.00) | 0.11% (1) | 128.00 (117.00, 140.00) | - |
| Heart rhythm | Regular rhythm | 61.78% (561) | - | 71.81% (242) | 0.30% (1) |
| | Sinus arrhythmia | 35.79% (325) | | 26.41% (89) | |
| | Other | 2.42% (22) | | 1.48% (5) | |
| LA:Ao | | 1.38 (1.26, 1.52) | - | 1.85 (1.72, 2.02) | - |
| LVIDDN (cm/kg$^{0.294}$) | | 1.52 (1.47, 1.70) | - | 1.93 (1.81, 2.11) | - |
| Murmur intensity | Soft | 25.55% (232) | 0.33% (3) | 4.45% (15) | - |
| | Moderate | 44.16% (401) | | 25.82% (87) | |
| | Loud | 24.89% (226) | | 48.66% (164) | |
| | Thrilling | 5.07% (46) | | 21.07% (71) | |
| Respiratory rate | | 26.00 (20.00, 32.00) | 12.44% (113) | 26.00 (22.00, 32.00) | 7.72% (26) |
| Serum biochemistry | Albumin (28-43 g/L) | 33.00 (31.00, 35.00) | - | 33.00 (30.00, 35.00) | - |
| | ALKP (14-147 U/L) | 52.50 (29.00, 125.00) | 0.11% (1) | 61.00 (33.00, 173.00) | - |
| | ALT (<122 U/L) | 48.00 (34.00, 76.00) | - | 51.00 (37.00, 76.00) | - |
| | Bilirubin (0-6.8 μmol/L) | 3.20 (2.40, 3.42) | 0.22% (2) | 3.10 (2.10, 3.42) | - |
| | BUN (3.2-10.3 mmol/L) | 6.10 (4.80, 7.85) | 0.11% (1) | 5.90 (5.00, 7.50) | - |

TABLE 2-continued

Clinicopathological data for dogs with stage B1 or stage B2 degenerative mitral valve disease. Descriptive statistics are reported for the clean dataset. cTnI, cardiac troponin I; NT-proBNP, N-terminal propeptide of B-type natriuretic peptide; ALKP, alkaline phosphatase; ALT, alanine aminotransferase; BUN, blood urea nitrogen; GGT, gamma-glutamyl transferase; SDMA, symmetric dimethylarginine; TS, total solids; VHS, vertebral heart score. A hyphen (-) is used to indicate that there were no missing data for this variable.

| Variable (Laboratory Reference Interval) | Population | | | |
| | B1 (n = 908) | Missing | B2 (n = 337) | Missing |
| --- | --- | --- | --- | --- |
| Calcium (2.1-2.9 mmol/L) | 2.50 (2.40, 2.60) | 0.22% (2) | 2.50 (2.40, 2.60) | - |
| Chloride (106-120 mmol/L) | 111.00 (109.00, 113.00) | - | 111.00 (109.00, 113.00) | - |
| Cholesterol (3.6-10.3 mmol/L) | 6.28 (5.20, 7.50) | 0.22% (2) | 5.90 (4.86, 7.12) | - |
| Creatinine (44-133 μmol/L) | 65.00 (53.04, 79.56) | - | 61.88 (52.00, 73.00) | - |
| GGT (<13 U/L) | 4.00 (3.00, 5.50) | 0.11% (1) | 4.00 (3.00, 6.00) | - |
| Globulin (24-43 g/L) | 30.00 (28.00, 33.00) | - | 30.00 (27.00, 33.00) | - |
| Glucose (3.2-7.0 mmol/L) | 5.30 (4.80, 5.71) | - | 5.30 (4.90, 5.66) | 0.30% (1) |
| Phosphate (0.9-1.7 mmol/L) | 1.20 (1.00, 1.40) | 0.11% (1) | 1.26 (1.10, 1.42) | - |
| Potassium (3.9-5.8 mmol/L) | 4.50 (4.30, 4.80) | 0.22% (2) | 4.60 (4.30, 4.90) | - |
| SDMA (0-14 μg/dL) | 10.00 (9.00, 13.00) | 0.99% (9) | 10.00 (9.00, 12.00) | 0.59% (2) |
| Sodium (142-153 mmol/L) | 148.00 (147.00, 150.00) | - | 148.00 (147.00, 150.00) | - |
| TS (54-76 g/L) | 63.00 (60.00, 66.25) | - | 63.00 (60.00, 66.00) | - |
| VHS (n = 175) | 10.80 (10.25, 11.10) | - | 11.50 (11.00, 12.25) | - |

TABLE 3

The results of the explanatory multivariable logistic regression model showing risk factors associated with having stage B2 DMVD. ALT, alanine aminotransferase; BCS, body condition score; NT-proBNP, N-terminal propeptide of β-type natriuretic peptide; $\log_{10}$, logarithmic transformation to the base 10; β, regression coefficient; CI, confidence intervals; P, statistical significance; e, multiply by $10^x$; a hyphen (-) indicates that this level was used as for comparisons.

| Variable | β | Odds Ratio (95% CIs) | P |
| --- | --- | --- | --- |
| Intercept | −23.91 | $4.07 \, e^{-11}$ ($4.59 \, e^{-16}$-$3.81 \, e^{-6}$) | <.001 |
| Age (≤8) | - | - | - |
| Age (8-10) | 0.34 | 1.41 (0.89-2.24) | .149 |
| Age (10-12) | −0.13 | 0.88 (0.54-1.44) | .614 |
| Age (>12) | −0.47 | 0.63 (0.36-1.10) | .106 |
| Appetite (Decreased) | 2.38 | 10.85 (2.60-53.31) | .002 |
| $\log_{10}$(ALT) | 7.45 | 1773.22 ($3.32$-$7.99 \, e^5$) | .018 |
| BCS (≤3) | - | - | - |
| BCS (4) | −1.70 | 0.18 (0.06-0.53) | .002 |
| BCS (5) | −1.32 | 0.27 (0.10-0.74) | .010 |
| BCS (6) | −0.90 | 0.41 (0.15-1.14) | .084 |
| BCS (7) | −1.69 | 0.19 (0.06-0.58) | .004 |
| BCS (≥8) | −1.98 | 0.14 (0.03-0.54) | .005 |
| Creatinine | −0.02 | 0.98 (0.97-0.99) | <.001 |
| Murmur (soft) | - | - | - |
| Murmur (moderate) | 0.94 | 2.57 (1.38-5.09) | .004 |
| Murmur (loud) | 1.82 | 6.19 (3.37-12.21) | <.001 |
| Murmur (thrilling) | 2.31 | 10.10 (4.81-22.32) | <.001 |
| $\log_{10}$(NT-proBNP) | 7.77 | 2374.40 ($49.23$-$1.12 \, e^5$) | <.001 |
| $\log_{10}$(ALT) * $\log_{10}$(NT-proBNP) | −2.25 | 0.10 (0.01-0.89) | .037 |

TABLE 4a-c

Pairwise comparisons of estimated marginal means for categorical variables in the multivariable model. BCS; Results are presented for the change in coefficients ($\Delta\beta = \beta$ level 1 − $\beta$ level 2) and significance of this pairwise comparison. Values were calculated with other variables held constant. BCS, body condition score; $\Delta\beta$, difference in coefficients; P, significance.

| Level 1 | Level 2 | $\Delta\beta$ (±standard error) | P |
|---|---|---|---|
| | | a: Age | |
| Age (≤8) | Age (8-10) | −0.34 (±0.24) | .149 |
| Age (≤8) | Age (10-12) | 0.13 (±0.25) | .614 |
| Age (≤8) | Age (>12) | 0.47 (±0.29) | .106 |
| Age (8-10) | Age (10-12) | 0.47 (±0.22) | .033 |
| Age (8-10) | Age (>12) | 0.81 (±0.26) | .002 |
| Age (10-12) | Age (>12) | 0.34 (±0.26) | .190 |
| | | b: Body condition score | |
| BCS (≤3) | BCS (4) | 1.70 (±0.54) | .002 |
| BCS (≤3) | BCS (5) | 1.32 (±0.51) | .010 |
| BCS (≤3) | BCS (6) | 0.90 (±0.52) | .084 |
| BCS (≤3) | BCS (7) | 1.69 (±0.58) | .004 |
| BCS (≤3) | BCS (≥8) | 1.98 (±0.71) | .005 |
| BCS (4) | BCS (5) | −0.38 (±0.25) | .125 |
| BCS (4) | BCS (6) | −0.80 (±0.27) | .003 |
| BCS (4) | BCS (7) | −0.01 (±0.37) | .969 |
| BCS (4) | BCS (≥8) | 0.28 (±0.54) | .612 |
| BCS (5) | BCS (6) | −0.42 (±0.21) | .040 |
| BCS (5) | BCS (7) | 0.37 (±0.33) | .259 |
| BCS (5) | BCS (≥8) | 0.66 (±0.52) | .202 |
| BCS (6) | BCS (7) | 0.79 (±0.34) | .020 |
| BCS (6) | BCS (≥8) | 1.08 (±0.52) | .039 |
| BCS (7) | BCS (≥8) | 0.29 (±0.59) | .618 |
| | | c: Murmur intensity | |
| Murmur (soft) | Murmur (moderate) | −0.94 (±0.33) | .004 |
| Murmur (soft) | Murmur (loud) | −1.82 (±0.33) | <.001 |
| Murmur (soft) | Murmur (thrilling) | −2.31 (±0.39) | <.001 |
| Murmur (moderate) | Murmur (loud) | −0.88 (±0.19) | <.001 |
| Murmur (moderate) | Murmur (thrilling) | −0.49 (±0.28) | <.001 |
| Murmur (loud) | Murmur (thrilling) | −1.37 (±0.29) | .076 |

Table 5: The performance of a series of models predicting preclinical disease status. AUC, area under the receiver operating characteristic curve; CI, confidence intervals; GBM, gradient boosting machine; RBF, radial basis function; SD, standard deviation; SVM, support vector machine.

TABLE 6

The results of a predictive logistic regression model fitted on the training data with features selected by backwards stepwise elimination. BCS, body condition score; NT-proBNP, N-terminal propeptide of B-type natriuretic peptide; log10, logarithmic transformation to the base 10; $\beta$, regression coefficient; CI, confidence intervals; P, statistical significance; e, multiply by 10x; a hyphen (-) indicates that this level was used as for comparisons.

| Variable | $\beta$ | Odds Ratio (95% CIs) | P |
|---|---|---|---|
| Intercept | −10.00 | $4.53e^{-5}$ ($4.26e^{-6}$-$4.33e^{-4}$) | <.001 |
| Appetite (Decreased) | 2.99 | 19.81 (3.73-154.60) | .001 |
| BCS (≤3) | - | - | - |
| BCS (4) | −1.83 | 0.16 (0.05-0.52) | .003 |
| BCS (5) | −1.39 | 0.25 (0.08-0.77) | .016 |
| BCS (6) | −1.11 | 0.33 (0.10-1.04) | .058 |
| BCS (7) | −1.58 | 0.21 (0.05-0.74) | .016 |
| BCS (≥8) | −2.01 | 0.13 (0.03-0.58) | .009 |
| Creatinine | −0.02 | 0.98 (0.97-0.99) | <.001 |
| Murmur (soft) | - | - | - |
| Murmur (moderate) | 0.73 | 2.07 (1.09-4.18) | .033 |
| Murmur (loud) | 1.59 | 4.89 (2.59-9.85) | <.001 |
| Murmur (thrilling) | 1.93 | 6.89 (3.19-15.61) | <.001 |
| $Log_{10}$(NT-proBNP) | 3.66 | 38.98 (19.38-81.56) | <.001 |

TABLE 7

Values of positive and negative predictive value for deciles of predicted probability produced by the predictive logistic regression model. CI, confidence interval; PPV, positive predictive value; NPV, negative predictive value. Positive predictive value represents the probability of being in stage B2, given a positive test result. Negative predictive value represents the probability of being in stage B1, given a negative test result.

| Predicted Probability | PPV (%) (95% CIs) | NPV (%) (95% CIs) |
|---|---|---|
| 0.10 | 38.89 (37.20-40.67) | 95.47 (92.69-97.72) |
| 0.20 | 47.50 (44.49-50.49) | 89.93 (87.35-92.41) |
| 0.30 | 55.30 (51.14-59.52) | 86.94 (84.56-89.23) |
| 0.40 | 62.28 (56.98-67.31) | 84.58 (82.48-86.68) |
| 0.50 | 71.51 (65.57-77.40) | 83.53 (81.61-85.40) |
| 0.60 | 78.20 (71.53-84.50) | 80.86 (79.18-82.60) |
| 0.70 | 86.25 (78.57-93.41) | 78.23 (76.86-79.76) |
| 0.80 | 86.11 (75.50-95.12) | 74.69 (73.77-75.76) |
| 0.90 | 1.00 (1.00-1.00) | 72.73 (72.21-73.34) |

TABLE 5

| | | Logistic Regression | | | | | | |
|---|---|---|---|---|---|---|---|---|
| | | Backwards stepwise elimination | Ridge regression | SVM linear | SVM polynomial | SVM RBF | Random Forest | GBM |
| Train (n = 848) | AUC (95% CI) | 0.83 (0.80-0.86) | 0.86 (0.83-0.88) | 0.84 (0.81-0.87) | 0.84 (0.81-0.87) | 0.94 (0.93-0.96) | 0.92 (0.90-0.94) | Train (n = 848) |
| | Accuracy | 0.81 | 0.83 | 0.82 | 0.82 | 0.87 | 0.84 | 0.85 |
| | Bootstrap AUC (SD) | 0.85 (0.024) | 0.86 (0.023) | 0.84 (0.026) | 0.84 (0.025) | 0.94 (0.015) | 0.92 (0.015) | 0.93 (0.015) |
| Test (n = 212) | AUC (95% CI) | 0.86 (0.81-0.91) | 0.88 (0.83-0.93) | 0.88 (0.83-0.92) | 0.87 (0.83-0.92) | 0.86 (0.81-0.91) | 0.85 (0.79-0.90) | Test (n = 212) |
| | Accuracy | 0.79 | 0.80 | 0.79 | 0.79 | 0.80 | 0.81 | 0.81 |
| | Brier score | 0.133 | 0.130 | 0.129 | 0.130 | 0.134 | 0.138 | 0.136 |
| | Calibration in the large | 0.133 | 0.053 | 0.079 | 0.083 | 0.059 | 0.128 | −0.009 |
| | Calibration slope | 0.802 | 0.897 | 0.817 | 0.811 | 0.900 | 0.731 | 0.930 |
| n(Variables Required) | | 5 | 26 | 26 | 26 | 26 | 26 | 26 |
| Interpretable | | Yes | Yes | No | No | No | No | No |

TABLE S1

Patient characteristics in the clean, complete and excluded populations. BCS, body condition score; CKCS, Cavalier King Charles Spaniel; ACEi, angiotensin converting enzyme inhibitor.

| Variable | | Population | | |
|---|---|---|---|---|
| | | Clean (n = 1245) | Complete (n = 1887) | Excluded (n = 642) |
| Age (years) | | 10.00 (8.03, 11.63) | 10.00 (8.17, 11.83) | 10.33 (8.27, 12.17) |
| BCS | ≤3 | 2.33% (29) | 2.65% (50) | 3.27% (21) |
| | 4 | 15.98% (199) | 16.59% (313) | 17.76% (114) |
| | 5 | 42.09% (524) | 421.92% (791) | 41.59% (267) |
| | 6 | 24.02% (299) | 23.04% (434) | 21.03% (135) |
| | 7 | 11.16% (139) | 11.13% (210) | 11.06% (71) |
| | ≥8 | 3.93% (49) | 6.6% (79) | 4.67% (30) |
| Breed | CKCS | 23.45% (292) | 25.33% (478) | 28.97% (186) |
| Cardiac medications | ACEi | 3.45% (43) | 10.28% (194) | 23.52% (151) |
| | Pimobendan | - | 19.13% (361) | 56.23% (361) |
| | Spironolactone | 0.72% (9) | 2.60% (49) | 6.23% (40) |
| Sex | Female entire | 3.69% (46) | 3.71% (70) | 3.74% (24) |
| | Female neutered | 38.63% (481) | 39.48% (745) | 41.12% (264) |
| | Male entire | 11.89% (148) | 12.13% (229) | 12.62% (81) |
| | Male neutered | 45.78% (570) | 44.67% (843) | 42.52% (273) |
| Weight (kg) | | 9.10 (6.60, 12.30) | 9.05 (6.50, 12.18) | 9.00 (6.30, 11.90) |

TABLE S2

Clinicopathological data for dogs included in the clean, complete and excluded populations. cTnI, cardiac troponin I; NT-proBNP, N-terminal propeptide of B-type natriuretic peptide; ALKP, alkaline phosphatase; ALT, alanine aminotransferase; BUN, blood urea nitrogen; GGT, gamma-glutamyl transferase, SDMA, symmetric dimethylarginine; TS, total solids; VHS, vertebral heart score.

| Variable (Laboratory Reference Interval) | | Population | | |
|---|---|---|---|---|
| | | Clean (n = 1245) | Complete (n = 1887) | Excluded (n = 642) |
| Appetite | Decreased | 1.20% (15) | 1.91% (36) | 3.27% (21) |
| Cardiac biomarkers | cTnI (ng/ml) | 0.05 (0.03, 0.09) | 0.05 (0.03, 0.09) | 0.05 (0.03, 0.10) |
| | NT-proBNP (pmol/L) | 687.00 (426.00, 1121.00) | 704.00 (427.00, 1171.00) | 731.50 (434.75, 1261.00) |
| Cough | Yes | 24.02% (299) | 25.86% (488) | 29.44% (189) |
| Disease stage | B2 | 27.07% (337) | 32.22% (608) | 42.21% (271) |
| Exercise tolerance | Decreased | 11.16% (139) | 11.39% (215) | 11.84% (76) |
| Heart rate | | 120.00 (108.00, 136.00) | 120.00 (108.00, 136.00) | 120.00 (108.00, 136.00) |
| Heart rhythm | Regular rhythm | 64.50% (803) | 64.86% (1224) | 65.58% (421) |
| | Sinus arrhythmia | 33.25% (414) | 33.12% (625) | 32.87% (211) |
| | Other | 2.17% (27) | 1.96% (37) | 1.56% (10) |
| LA:Ao | | 1.48 (1.31, 1.71) | 1.52 (1.33, 1.75) | 1.60 (1.39, 1.83) |
| LVIDDN (cm/kg$^{0.294}$) | | 1.67 (1.52, 1.84) | 1.71 (1.54, 1.89) | 1.78 (1.60, 1.96) |
| Murmur intensity | Soft | 19.84% (247) | 17.22% (325) | 12.15% (78) |
| | Moderate | 39.20% (488) | 36.25% (684) | 30.53% (196) |
| | Loud | 31.33% (390) | 34.82% (657) | 41.59% (267) |
| | Thrilling | 9.40% (117) | 11.55% (218) | 15.73% (101) |
| Respiratory rate | | 26.00 (20.00, 32.00) | 25.00 (20.00, 32.00) | 24.00 (22.00, 32.00) |
| Serum biochemistry | Albumin (28-43 g/L) | 33.00 (31.00, 35.00) | 33.00 (31.00, 35.00) | 33.00 (31.00, 35.00) |
| | ALKP (14-147 U/L) | 55.00 (30.00, 139.00) | 57.00 (30.00, 146.75) | 61.00 (31.00, 176.00) |
| | ALT (<122 U/L) | 49.00 (35.00, 76.00) | 51.00 (35.00, 78.00) | 55.00 (36.00, 87.00) |
| | Bilirubin (0-6.8 μmol/L) | 3.20 (2.20, 3.42) | 3.20 (2.40, 3.42) | 3.20 (2.40, 3.42) |
| | BUN (3.2-10.3 mmol/L) | 6.07 (4.88, 7.70) | 6.10 (4.90, 7.90) | 6.41 (5.00, 8.57) |
| | Calcium (2.1-2.9 mmol/L) | 2.50 (2.40, 2.60) | 2.50 (2.40, 2.60) | 2.50 (2.40, 2.60) |

TABLE S2-continued

Clinicopathological data for dogs included in the clean, complete and excluded
populations. cTnI, cardiac troponin I; NT-proBNP, N-terminal propeptide of B-type
natriuretic peptide; ALKP, alkaline phosphatase; ALT, alanine aminotransferase; BUN,
blood urea nitrogen; GGT, gamma-glutamyl transferase, SDMA, symmetric
dimethylarginine; TS, total solids; VHS, vertebral heart score.

| | Population | | |
| Variable (Laboratory Reference Interval) | Clean (n = 1245) | Complete (n = 1887) | Excluded (n = 642) |
| --- | --- | --- | --- |
| Chloride (106-120 mmol/L) | 111.00 (109.00, 113.00) | 111.00 (109.00, 113.00) | 111.00 (109.00, 113.00) |
| Cholesterol (3.6-10.3 mmol/L) | 6.19 (5.10, 7.40) | 6.20 (5.10, 7.50) | 6.30 (5.20, 7.70) |
| Creatinine (44-133 μmol/L) | 64.00 (53.04, 79.00) | 64.00 (53.04, 79.56) | 65.00 (53.04, 79.56) |
| GGT (<13 U/L) | 4.00 (3.00, 6.00) | 4.00 (3.00, 6.00) | 4.00 (3.00, 6.00) |
| Globulin (24-43 g/L) | 30.00 (28.00, 33.00) | 30.00 (28.00, 33.00) | 30.00 (28.00, 33.00) |
| Glucose (3.2-7.0 mmol/L) | 5.30 (4.80, 5.70) | 5.30 (4.80, 5.71) | 5.26 (4.70, 5.77) |
| Phosphate (0.9-1.7 mmol/L) | 1.20 (1.00, 1.40) | 1.20 (1.03, 1.40) | 1.29 (1.10, 1.50) |
| Potassium (3.9-5.8 mmol/L) | 4.50 (4.30, 4.80) | 4.50 (4.30, 4.80) | 4.60 (4.30, 4.80) |
| SDMA (0-14 μg/dL) | 10.00 (9.00, 12.00) | 10.00 (9.00, 13.00) | 11.00 (9.00, 13.00) |
| Sodium (142-153 mmol/L) | 148.00 (147.00, 150.00) | 148.00 (147.00, 150.00) | 148.00 (147.00, 150.00) |
| TS (54-76 g/L) | 63.00 (60.00, 66.00) | 63.00 (60.00, 66.00) | 63.00 (59.00, 66.00) |
| VHS | 11.00 (10.50, 11.50) | 11.00 (10.50, 11.80) | 11.15 (10.50, 12.00) |

Example 2

Example 2 provides further details of the ridge regression analysis described in Example 1. For this analysis, one hot encoding was used to work within the Scikit-Learn library in Python. Lambda was tuned to minimise the Brier score averaged over 5 cross validation loops on the training set. The intercept was −1.226.

| Variable | Coefficient |
| --- | --- |
| $Log_{10}$(ALKP) | 0.041 |
| $Log_{10}$(ALT) | 0.095 |
| Albumin | 0.113 |
| Blood urea nitrogen (BUN) | −0.120 |
| Calcium | 0.003 |
| Chloride | −0.103 |
| Creatinine | −0.125 |
| Cholesterol | −0.111 |
| Globulin | 0.068 |
| Glucose | 0.092 |
| Potassium | 0.069 |
| Phosphate | 0.107 |
| SDMA | −0.125 |
| Sodium | −0.002 |
| Appetite (decreased) | 0.225 |
| Cough (yes) | 0.076 |
| Exercise tolerance (decreased) | 0.084 |
| Heart rate | 0.072 |
| Logio (NT-proBNP) | 0.872 |
| Breed (CKCS) | −0.076 |
| Bilirubin (2.2 < x ≤ 3.2) | 0.041 |
| Bilirubin (3.2 < x ≤ 3.4) | 0.099 |
| Bilirubin (x ≤ 2.2) | 0.041 |
| Bilirubin (x > 3.4) | −0.119 |
| GGT(3 < x ≤ 4) | −0.113 |
| GGT (4 < x ≤ 6) | 0.020 |
| GGT (x ≤ 3) | 0.036 |
| GGT (x > 6) | 0.052 |
| BCS (≤3) | 0.168 |
| BCS (4) | −0.089 |
| BCS (5) | 0.031 |
| BCS (6) | 0.096 |
| BCS (7) | −0.072 |

-continued

| Variable | Coefficient |
| --- | --- |
| BCS (>=8) | −0.142 |
| cTnI (0.03 < x ≤ 0.05) | −0.009 |
| cTnI (0.05 < x ≤ 0.08) | 0.084 |
| cTnI (x ≤ 0.03) | −0.033 |
| cTnI (x > 0.08) | −0.039 |
| Heart rhythm (other) | −0.047 |
| Heart rhythm (sinus rhythm) | 0.067 |
| Heart rhythm (sinus arrhythmia) | −0.054 |
| Murmur grade (loud) | 0.233 |
| Murmur grade (moderate) | −0.135 |
| Murmur grade (soft) | −0.286 |
| Murmur grade (thrilling) | 0.242 |
| Respiratory rate (20 < x ≤ 26) | 0.034 |
| Respiratory rate (26 < x ≤ 32) | −0.086 |
| Respiratory rate (x ≤ 20) | 0.065 |
| Respiratory rate (x > 32) | −0.009 |
| Age (10 < x ≤ 12) | −0.022 |
| Age (8 < x ≤ 10) | 0.115 |
| Age (x ≤ 8) | −0.019 |
| Age (x > 12) | −0.092 |
| Sex (FE) | −0.085 |
| Sex (FN) | −0.013 |
| Sex (ME) | 0.003 |
| Sex (MN) | 0.045 |

For an animal with a decreased appetite, cough, decreased exercise tolerance, bilirubin (>3.4), GGT (>6), BCS (3), cTnI (>0.08), heart rhythm (sinus rhythm), a thrilling murmur, respiratory rate (>32), age (>12), sex (MN)

$$Odds=Exp[-1.226+(log_{10}(ALKP)\times0.041)+(log_{10}(ALT)\times0.095)+(Albumin\times0.113)+(BUN\times-0.120)+(Calcium\times0.003)+(Chloride\times-0.103)+(Creatinine\times-0.125)+(Cholesterol\times-0.111)+(Globulin\times0.068)+(Glucose\times0.092)+(Potassium\times0.069)+(Phosphate\times0.107)+(SDMA\times-0.125)+(Sodium\times-0.002)+(0.225)+(0.076)+(0.084)+(heart\ rate\times0.072)+(log_{10}(NT-proBNP)\times0.872)+(-0.119)+(0.052)+(0.168)+(-0.039)+(0.067)+(0.242)+(-0.009)+(-0.092)+(0.045)]$$

Predicted probability=Odds/[1+Odds]

37

The equation will change depending on the categorical variables selected. The coefficients may change if lambda is re-tuned.

REFERENCES

1. Fox P R. Pathology of myxomatous mitral valve disease in the dog. J Vet Cardiol. 2012; 14(1): 103-26.

2. Egenvall A, Bonnett B N, Hedhammar Å, Olson P. Mortality in over 350,000 insured Swedish dogs from 1995-2000: II. Breed-specific age and survival patterns and relative risk for causes of death. Acta Vet Scand. 2005; 46(3): 121-36.

3. Mattin M J, Boswood A, Church D B, McGreevy P D, O'Neill D G, Thomson P C, et al. Degenerative mitral valve disease: Survival of dogs attending primary-care practice in England. Prey Vet Med. 2015; 122(4): 436-42.

4. Keene B W, Atkins C E, Bonagura J D, Fox P R, Häggström J, Fuentes V L, et al. ACVIM consensus guidelines for the diagnosis and treatment of myxomatous mitral valve disease in dogs. J Vet Intern Med. 2019 May 11; 33(3): 1127-40.

5. Boswood A, Häggström J, Gordon S G, Wess G, Stepien R L, Oyama M A, et al. Effect of Pimobendan in Dogs with Preclinical Myxomatous Mitral Valve Disease and Cardiomegaly: The EPIC Study-A Randomized Clinical Trial. J Vet Intern Med. 2016 Nov; 30(6): 1765-79.

6. Patronek G J, Waters D J, Glickman L T. Comparative longevity of pet dogs and humans: Implications for gerontology research. Journals Gerontol—Ser A Biol Sci Med Sci. 1997 May 1; 52(3): 171-8.

7. Boswood A, Gordon S G, Häggström J, Wess G, Stepien R L, Oyama M A, et al. Longitudinal Analysis of Quality of Life, Clinical, Radiographic, Echocardiographic, and Laboratory Variables in Dogs with Preclinical Myxomatous Mitral Valve Disease Receiving Pimobendan or Placebo: The EPIC Study. J Vet Intern Med. 2018 Dec. 6; 32(1): 72-85.

8. Borgarelli M, Crosara S, Lamb K, Savarino P, La Rosa G, Tarducci A, et al. Survival Characteristics and Prognostic Variables of Dogs with Preclinical Chronic Degenerative Mitral Valve Disease Attributable to Myxomatous Degeneration. J Vet Intern Med. 2012 Jan; 26(1): 69-75.

9. Mattin M J, Brodbelt D C, Church D B, Boswood A. Factors associated with disease progression in dogs with presumed preclinical degenerative mitral valve disease attending primary care veterinary practices in the United Kingdom. J Vet Intern Med. 2019 Mar. 1; 33(2): 445-54.

10. Eriksson A S, Häggström J, Pedersen H D, Hansson K, Järvinen A-K, Haukka J, et al. Increased NT-proANP predicts risk of congestive heart failure in Cavalier King Charles spaniels with mitral regurgitation caused by myxomatous valve disease. J Vet Cardiol. 2014 Sep. 1; 16(3): 141-54.

11. Pedersen H D, Häggström J, Falk T, Mow T, Olsen L H, Iversen L, et al. Auscultation in Mild Mitral Regurgitation in Dogs: Observer Variation, Effects of Physical Maneuvers, and Agreement with Color Doppler Echocardiography and Phonocardiography. J Vet Intern Med. 1999 Jan. 1; 13(1): 56-64.

12. Häggström J, Kvart C, Hansson K. Heart Sounds and Murmurs: Changes Related to Severity of Chronic Valvular Disease in the Cavalier King Charles Spaniel. J Vet Intern Med. 1995; 9(2): 75-85.

13. Ljungvall I, Ahlstrom C, Höglund K, Hult P, Kvart C, Borgarelli M, et al. Use of signal analysis of heart sounds and murmurs to assess severity of mitral valve regurgitation attributable to myxomatous mitral valve disease in dogs. Am J Vet Res. 2009; 70(5): 604-13.

14. Ljungvall I, Rishniw M, Porciello F, Ferasin L, Ohad D G. Murmur intensity in small-breed dogs with myxomatous mitral valve disease reflects disease severity. J Small Anim Pract. 2014; 55(11): 545-50.

15. Kvart C, Häggström J, Pedersen H D, Hansson K, Eriksson A, Järvinen A-K, et al. Efficacy of enalapril for prevention of congestive heart failure in dogs with myxomatous valve disease and asymptomatic mitral regurgitation. J Vet Intern Med. 2002; 16(1): 80-8.

16. Oyama M A, Rush J E, O'Sullivan M L, Williams R M, Rozanski E A, Petrie J P, et al. Perceptions and priorities of owners of dogs with heart disease regarding quality versus quantity of life for their pets. J Am Vet Med Assoc. 2008 Jul. 1; 233(1): 104-8.

17. Chetboul V, Athanassiadis N, Concordet D, Nicolle A, Tessier D, Castagnet M, et al. Observer-dependent variability of quantitative clinical endpoints: the example of canine echocardiography. J Vet Pharmacol Ther. 2004 Feb; 27(1): 49-56.

18. Moonarmart W, Boswood A, Fuentes V L, Brodbelt D, Souttar K, Elliott J. N-terminal pro B-type natriuretic peptide and left ventricular diameter independently predict mortality in dogs with mitral valve disease. J Small Anim Pract. 2010 Feb 1; 51(2): 84-96.

19. Serres F, Pouchelon J-L, Poujol L, Lefebvre H P, Trumel C, Daste T, et al. Plasma N-terminal pro-B-type natriuretic peptide concentration helps to predict survival in dogs with symptomatic degenerative mitral valve disease regardless of and in combination with the initial clinical status at admission. J Vet Cardiol. 2009 Dec; 11(2): 103-21.

20. Oyama M A, Sisson D D. Cardiac troponin-I concentration in dogs with cardiac disease. J Vet Intern Med. 2004; 18(6): 831-9.

21. Spratt D P, Mellanby R J, Drury N, Archer J. Cardiac troponin I: evaluation I of a biomarker for the diagnosis of heart disease in the dog. J Small Anim Pract. 2005 Mar; 46(3): 139-45.

22. Ljungvall I, Höglund K, Tidholm A, Olsen L H, Borgarelli M, Venge P, et al. Cardiac troponin I is associated with severity of myxomatous mitral valve disease, age, and C-reactive protein in dogs. J Vet Intern Med. 2010 Jan. 1; 24(1): 153-9.

23. Hezzell M J, Boswood A, Chang Y-M, Moonarmart W, Souttar K, Elliott J. The Combined Prognostic Potential of Serum High-Sensitivity Cardiac Troponin I and N-Terminal pro-B-Type Natriuretic Peptide Concentrations in Dogs with Degenerative Mitral Valve Disease. J Vet Intern Med. 2016; 26(2): 302-11.

24. Mattin M J, Boswood A, Church D B, Brodbelt D C. Prognostic factors in dogs with presumed degenerative mitral valve disease attending primary-care veterinary practices in the United Kingdom. Journal of Veterinary Internal Medicine. 2019 Dec. 18; 432-44.

25. Peduzzi P, Concato J, Kemper E, Holford T R, Feinstem A R. A simulation study of the number of events per variable in logistic regression analysis. J Clin Epidemiol. 1996 Dec. 1; 49(12): 1373-9.

26. Chapman S E, Hostutler R A. A Laboratory Diagnostic Approach to Hepatobiliary Disease in Small Animals. Vol. 43, Veterinary Clinics of North America—Small Animal Practice. 2013. p. 1209-25.

27. Levine S A. Notes on the Gradation of the Intensity of Cardiac Murmurs. JAMA J Am Med Assoc. 1961 Jul. 29; 177(4): 261.

28. American Animal Hospital Association. Canine Body Condition Score for 1-9 and 1-5 Scales. Veterinary Forensics: Animal Cruelty Investigations. 2013.

29. Hansson K, Häggström J, Kvart C, Lord P. Left atrial to aortic root indices using two-dimensional and M-mode echocardiography in cavalier King Charles Spaniels with and without left atrial enlargement. Vet Radiol Ultrasound. 2002; 43(6): 568-75.

30. Thomas W P, Gaber C E, Jacobs G J, Kaplan P M, Lombard C W, Sydney Moise N, et al. Recommendations for Standards in Transthoracic Two-Dimensional Echocardiography in the Dog and Cat. Vet Radiol Ultrasound. 1994; 35(3): 173-8.

31. Cornell C C, Kittleson M D, Della Torre P, Häggström J, Lombard C W, Pedersen H D, et al. Allometric Scaling of M-Mode Cardiac Measurements in Normal Adult Dogs. J Vet Intern Med. 2004; 18(1): 311-21.

32. Buchanan J W, Bücheler J. Vertebral scale system to measure canine heart size in radiographs. J Am Vet Med Assoc. 1995 Jan. 15; 206(2): 194-9.

33. Hansson K, Häggström J, Kvart C, Lord P. Interobserver variability of vertebral heart size measurements in dogs with normal and enlarged hearts. Vet Radiol Ultrasound. 2005; 46(2): 122-30.

34. Dohoo I R, Martin S W, Stryhn H. Veterinary epidemiologic research. No. V413. Charlottetown, Canada: AVC Inc; 2003.706 p.

35. Royston P, Sauerbrei W. Multivariable Model-Building: A Pragmatic Approach to Regression Analysis based on Fractional Polynomials for Modelling Continuous Variables. Multivariable Model-Building: A Pragmatic Approach to Regression Analysis based on Fractional Polynomials for Modelling Continuous Variables. Wiley Blackwell; 2008.1-303 p.

36. Hosmer D W, Lemeshow S, Sturdivant R X. Applied Logistic Regression. Third. John Wiley & Sons, Ltd; 2013.

37. DeLong E R, DeLong D M, Clarke-Pearson D L. Comparing the Areas under Two or More Correlated Receiver Operating Characteristic Curves: A Nonparametric Approach. Biometrics. 1988 Sep; 44(3): 837.

38. Hoerl A E, Kennard R W. Ridge Regression: Biased Estimation for Nonorthogonal Problems. Technometrics. 1970; 12(1): 55-67.

39. Cortes C, Vapnik V. Support-vector networks. Mach Learn. 1995 Sep; 20(3): 273-97.

40. Breiman L. Random forests. Mach Learn. 2001 Oct; 45(1): 5-32.

41. Chen T, Guestrin C. XGBoost: A scalable tree boosting system. In: Proceedings of the ACM SIGKDD International Conference on Knowledge Discovery and Data Mining. New York, New York, USA: Association for Computing Machinery; 2016. p. 785-94.

42. Efron B, Tibshirani R J. An Introduction to the Bootstrap. Chapman & Hall/CRC; 1993.

43. Kulesa A, Krzywinski M, Blainey P, Altman N. Points of Significance: Sampling distributions and the bootstrap. Nat Methods. 2015 May 28; 12(6): 477-8.

44. Steyerberg E W, Vickers A J, Cook NR, Gerds T, Gonen M, Obuchowski N, et al. Assessing the performance of prediction models: A framework for traditional and novel measures. Vol. 21, Epidemiology. 2010. p. 128-38.

45. Walsh C G, Sharman K, Hripcsak G. Beyond discrimination: A comparison of calibration methods and clinical usefulness of predictive models of readmission risk. J Biomed Inform. 2017 Dec. 1; 76: 9-18.

46. Steyerberg E W, Vergouwe Y. Towards better clinical prediction models: seven steps for development and an ABCD for validation. Eur Heart J. 2014 Aug. 1; 35(29): 1925-31.

47. Bonnett L J, Snell K I E, Collins G S, Riley R D. Guide to presenting clinical prediction models for use in clinical settings. BMJ. 2019 Apr. 17; 365.

48. Lopez-Alvarez J, Elliott J, Pfeiffer D, Chang Y-M, Mattin M, Moonarmart W, et al. Clinical Severity Score System in Dogs with Degenerative Mitral Valve Disease. J Vet Intern Med. 2015; 29: 575-81.

49. Collins G S, de Groot J A, Dutton S, Omar O, Shanyinde M, Tajar A, et al. External validation of multivariable prediction models: a systematic review of methodological conduct and reporting. BMC Med Res Methodol. 2014 Dec. 19; 14(1): 40.

50. Hezzell M J, Boswood A, Moonarmart W, Elliott J. Selected echocardiographic variables change more rapidly in dogs that die from myxomatous mitral valve disease. J Vet Cardiol. 2012; 14: 269-79.

51. Chetboul V, Serres F, Tissier R, Lefebvre H P P, Sampedrano C C, Gouni V, et al. Association of Plasma N-Terminal Pro-B-Type Natriuretic Peptide Concentration with Mitral Regurgitation Severity and Outcome in Dogs with Asymptomatic Degenerative Mitral Valve Disease. J Vet Intern Med. 2009 Sep; 23(5): 984-94.

52. Oyama M A, Boswood A, Connolly D J, Ettinger S J, Fox P R, Gordon S G, et al. Clinical usefulness of an assay for measurement of circulating n-terminal pro-b-type natriuretic peptide concentration in dogs and cats with heart disease. J Am Vet Med Assoc. 2013 Jul. 1; 243(1): 71-82.

53. Kellihan H B, Oyama M A, Reynolds C A, Stepien R L. Weekly variability of plasma and serum NT-proBNP measurements in normal dogs. J Vet Cardiol. 2009 May; 11(Supplementary Materials): 93-7.

54. Winter R L, Saunders A B, Gordon S G, Buch J S, Miller M W. Biologic variability of N-terminal pro-brain natriuretic peptide in healthy dogs and dogs with myxomatous mitral valve disease. J Vet Cardiol. 2017 Apr; 19(2): 124-31.

55. Höglund K, French A, Dukes-McEwan J, Häggström J, Smith P, Corcoran B, et al. Low intensity heart murmurs in boxer dogs: Inter-observer variation and effects of stress testing. J Small Anim Pract. 2004 Apr; 45(4): 178-85.

56. Keren R, Tereschuk M, Luan X. Evaluation of a Novel Method for Grading Heart Murmur Intensity. Arch Pediatr Adolesc Med. 2005 Apr. 1; 159(4): 329.

57. Fudim M, Wagman G, Altschul R, Yucel E, Bloom M, Vittorio T J. Pathophysiology and treatment options for cardiac anorexia. Curr Heart Fail Rep. 2011 Jun; 8(2): 147-53.

58. Fonfara S, Hetzel U, Tew S R, Dukes-Mcewan J, Cripps P, Clegg P D. Leptin Expression in Dogs with Cardiac Disease and Congestive Heart Failure. J Vet Intern Med. 2011 Sep; 25(5): 1017-24.

59. Adlbrecht C, Kommata S, Hulsmann M, Szekeres T, Bieglmayer C, Strunk G, et al. Chronic heart failure leads to an expanded plasma volume and pseudoanaemia, but does not lead to a reduction in the body's red cell volume. Eur Heart J. 2008 Oct. 1; 29(19): 2343-50.

60. Androne A-S, Katz S D, Lund L, LaManca J, Hudaihed A, Hryniewicz K, et al. Hemodilution is common in patients with advanced heart failure. Circulation. 2003 Jan. 21; 107(2): 226-9.

61. Abramov D, Cohen R S, Katz S D, Mancini D, Maurer M S. Comparison of blood volume characteristics in anemic patients with low versus preserved left ventricular ejection fractions. Am J Cardiol. 2008 Oct. 15; 102(8): 1069-72.

62. Duarte K, Monnez J M, Albuisson E, Pitt B, Zannad F, Rossignol P. Prognostic Value of Estimated Plasma Volume in Heart Failure. JACC Heart Fail. 2015 Nov. 1; 3(11): 886-93.

63. Dittrich S, Schuth A, Aurich H, vonLoeper J, Grosse-Siestrup C, Lange P E. Haemodilution improves organ function during normothermic cardiopulmonary bypass: investigations in isolated perfused pig kidneys. Perfusion. 2000 Jun; 15(3): 225-9.

64. Horn M A, Trafford A W. Aging and the cardiac collagen matrix: Novel mediators of fibrotic remodelling. Vol. 93, Journal of Molecular and Cellular Cardiology. Academic Press; 2016. p. 175-85.

65. Hezzell M J, Falk T, Olsen L H, Boswood A, Elliott J. Associations between N-terminal procollagen type III, fibrosis and echocardiographic indices in dogs that died due to myxomatous mitral valve disease. J Vet Cardiol. 2014 Dec; 16(4): 257-64.

66. Bay M, Kirk V, Parner J, Hassager C, Nielsen H, Krogsgaard K, et al. NT-proBNP: A new diagnostic screening tool to differentiate between patients with normal and reduced left ventricular systolic function. Heart. 2003; 89(2): 150-4.

67. Nikolaou M, Parissis J, Yilmaz M B, Seronde M F, Kivikko M, Laribi S, et al. Liver function abnormalities, clinical profile, and outcome in acute decompensated heart failure. Eur Heart J. 2013 Mar; 34(10): 742-9.

68. Kubo S H, Walter B A, John D H A, Clark M, Cody R J. Liver Function Abnormalities in Chronic Heart Failure: Influence of Systemic Hemodynamics. Arch Intern Med. 1987; 147(7): 1227-30.

69. Henriksen J H, Gøtze J P, Fuglsang S, Christensen E, Bendtsen F, Møller S. Increased circulating pro-brain natriuretic peptide (proBNP) and brain natriuretic peptide (BNP) in patients with cirrhosis: Relation to cardiovascular dysfunction and severity of disease. Gut. 2003 Oct. 1; 52(10): 1511-7.

70. Licata A, Corrao S, Petta S, Genco C, Cardillo M, Calvaruso V, et al. NT Pro BNP Plasma Level and Atrial Volume Are Linked to the Severity of Liver Cirrhosis. Vinciguerra M, editor. PLoS One. 2013 Aug. 5; 8(8): e68364.

71. Cawley G C, Talbot N L C. On over-fitting in model selection and subsequent selection bias in performance evaluation. Vol. 11, Journal of Machine Learning Research. 2010.

72. Rajkomar A, Dean J, Kohane I. Machine Learning in Medicine. N Engl J Med. 2019 Apr. 4; 380(14): 1347-58.

73. Steyerberg E W, van der Ploeg T, Van Calster B. Risk prediction with machine learning and regression methods. Vol. 56, Biometrical Journal. Wiley-VCH Verlag; 2014. p. 601-6.

74. Reagan K L, Reagan B A, Gilor C. Machine learning algorithm as a diagnostic tool for hypoadrenocorticism in dogs. Domest Anim Endocrinol. 2020 Jul. 1; 72: 106396.

75. Bradley R, Tagkopoulos I, Kim M, Kokkinos Y, Panagiotakos T, Kennedy J, et al. Predicting early risk of chronic kidney disease in cats using routine clinical laboratory tests and machine learning. J Vet Intern Med. 2019 Nov. 1; 33(6): 2644-56.

76. Bille C, Auvigne V, Libermann S, Bomassi E, Durieux P, Rattez E. Risk of anaesthetic mortality in dogs and cats: An observational cohort study of 3546 cases. Vet Anaesth Analg. 2012; 39(1): 59-68.

77. Collins G S, Ogundimu E O, Altman D G. Sample size considerations for the external validation of a multivariable prognostic model: A resampling study. Stat Med. 2016 Jan. 30; 35(2): 214-26.

78. Riley R D, Ensor J, Snell K I E, Debray T P A, Altman D G, Moons K G M, et al. External validation of clinical prediction models using big datasets from e-health records or IPD meta-analysis: Opportunities and challenges. BMJ. 2016; 353.

What is claimed is:

1. A method of diagnosing or screening for stage B2 degenerative mitral valve disease (DMVD) in a dog, the method comprising the steps of:
   (a) receiving characteristic data relating to the dog, the characteristic data comprising appetite, creatinine concentration, murmur intensity, and NT-proBNP concentration; and
   (b) processing the characteristic data using a model, wherein an output of the model is an output value associated with the probability of the dog having stage B2 DMVD.

2. The method of claim 1, wherein the dog has received a diagnosis of DMVD prior to step (a).

3. The method of claim 1, wherein the model is derived using a regression process.

4. The method of claim 3, wherein the model is derived using multivariable logistic regression or regularised regression.

5. The method of claim 1, wherein the model is derived using a machine learning process.

6. The method of claim 5, wherein the model is derived using a support vector machines (SVM) process, a random forest process, or a gradient boosting process.

7. A non-transitory computer-readable medium comprising code that, when executed by a computer system, instructs the computer system to perform the method of claim 1.

8. The method of claim 1, further comprising:
   (c) diagnosing the presence or absence of stage B2 DMVD in the dog based on a comparison of the output value to a predetermined value.

9. The method of claim 8, wherein the presence of stage B2 DMVD is indicated by an output value associated with a probability of the dog having stage B2 DMVD of greater than or equal to 0.872, and the absence of stage B2 DMVD is indicated by an output value associated with a probability of the dog having stage B2 DMVD of less than 0.106.

10. A method of training a model to predict stage B2 DMVD in a dog, the method comprising:
   (i) processing characteristic data relating to a dog using the model to output an output value, the characteristic data comprising appetite, creatinine concentration, murmur intensity, and NT-proBNP concentration;
   (ii) comparing the output value to a diagnosis of presence or absence of stage B2 DMVD in the dog; and
   (iii) adjusting the parameters of the model based on the result of the comparison.

11. The method of claim 10, wherein the diagnosis of presence or absence of stage B2 DMVD is based on echocardiographic examination.

12. The method of claim 10, further comprising:
   (iv) repeating steps (i) to (iii) one or more times, wherein the characteristic data relate to a different dog each time steps (i) to (iii) are performed.

13. The method of claim 10, wherein the model is derived using a regression process.

14. The method of claim 13, wherein the model is derived using multivariable logistic regression or regularised regression.

15. The method of claim 10, wherein the model is derived using a machine learning process.

16. The method of claim 15, wherein the model is derived using a support vector machines (SVM) process, a random forest process, or a gradient boosting process.

17. A non-transitory computer-readable medium comprising code that, when executed by a computer system, instructs the computer system to perform the method of claim 10.

18. A system for diagnosing stage B2 DMVD in dogs, the system comprising:

an input device configured to receive characteristic data relating to a dog, the characteristic data comprising appetite, creatinine concentration, murmur intensity, and NT-proBNP concentration;

a model configured to receive the characteristic data and generate an output value associated with the probability of the dog having stage B2 DMVD; and an output device configured to output the output value.

* * * * *